United States Patent
Tanouchi et al.

(10) Patent No.: US 11,688,487 B2
(45) Date of Patent: Jun. 27, 2023

(54) SCALABLE EXPERIMENTAL WORKFLOW FOR PARAMETER ESTIMATION

(71) Applicant: X Development LLC, Mountain View, CA (US)

(72) Inventors: Yu Tanouchi, Mountain View, CA (US); Nicholas Ruggero, Sunnyvale, CA (US)

(73) Assignee: X Development LLC, Mountain View, CA (US)

( * ) Notice: Subject to any disclaimer, the term of this patent is extended or adjusted under 35 U.S.C. 154(b) by 1001 days.

(21) Appl. No.: 16/527,380

(22) Filed: Jul. 31, 2019

(65) Prior Publication Data
US 2021/0035655 A1 Feb. 4, 2021

(51) Int. Cl.
*G16B 5/00* (2019.01)
*G16B 40/00* (2019.01)
*C12M 1/34* (2006.01)

(52) U.S. Cl.
CPC .............. *G16B 5/00* (2019.02); *C12M 41/32* (2013.01); *C12M 41/36* (2013.01); *C12M 41/46* (2013.01); *G16B 40/00* (2019.02)

(58) Field of Classification Search
CPC ...... C12M 41/48; C12M 41/36; C12M 41/46; C12M 41/32; G16B 5/30; G16B 40/00; G16B 5/00
See application file for complete search history.

(56) References Cited

U.S. PATENT DOCUMENTS

| | | | | |
|---|---|---|---|---|
| 5,442,562 A | * | 8/1995 | Hopkins | G05B 21/02 700/28 |
| 5,469,361 A | * | 11/1995 | Moyne | G05B 19/41845 700/95 |
| 7,062,417 B2 | * | 6/2006 | Kruger | G06F 17/18 703/2 |

(Continued)

FOREIGN PATENT DOCUMENTS

| | | |
|---|---|---|
| WO | 2006/060214 A2 | 6/2006 |
| WO | 2018/152442 A1 | 8/2018 |

OTHER PUBLICATIONS

International Search Report and Written Opinion dated Oct. 26, 2020 in related application No. PCT/US2020/044541, all pgs.

*Primary Examiner* — Shogo Sasaki
(74) *Attorney, Agent, or Firm* — Kilpatrick Townsend & Stockton LLP

(57) ABSTRACT

The present disclosure relates to a scalable experimental workflow that uses a culture system to maintain a steady state in a biological system, and techniques for identifying values for parameters in a in silico model based on experimental data obtained from the biological system. Particularly, aspects of the present disclosure are directed to obtaining measurement data for one or more characteristics of a biological system developed in a culture system, where the measurement data is indicative of each of the one or more characteristics at a physiological steady state where growth of the biological system is occurring at a substantially constant growth rate, determining a value for a parameter of a model of the biological system based on an growth formula, the measurement data, and the substantially constant growth rate, and parametrizing the model with at least the value determined for the parameter.

17 Claims, 9 Drawing Sheets

(56) References Cited

U.S. PATENT DOCUMENTS

| | | | | |
|---|---|---|---|---|
| 7,107,491 B2* | 9/2006 | Graichen | | G06F 11/008 |
| | | | | 714/48 |
| 8,818,562 B2* | 8/2014 | Bluck | | C12M 41/00 |
| | | | | 436/24 |
| 2009/0164171 A1* | 6/2009 | Wold | | G06F 17/18 |
| | | | | 702/179 |
| 2009/0287320 A1* | 11/2009 | MacGregor | | G05B 17/02 |
| | | | | 700/29 |
| 2010/0191361 A1* | 7/2010 | McCready | | G05B 13/048 |
| | | | | 703/2 |
| 2013/0095566 A1 | 4/2013 | Oltvai et al. | | |
| 2022/0228097 A1* | 7/2022 | White | | C12M 41/44 |
| 2022/0228102 A1* | 7/2022 | Le | | G16B 40/00 |

\* cited by examiner

SCALABLE EXPERIMENTAL WORKFLOW FOR PARAMETER ESTIMATION

FIELD

The present disclosure relates to a scalable experimental workflow for parameter estimation, and in particular to a scalable experimental workflow that uses a culture system to maintain a steady state in a biological system, and techniques for identifying values for parameters in a in silico model based on experimental data obtained from the biological system.

BACKGROUND

A biological system such as a living cell, or a population of living cells, can be modeled in silico such that the response of the living cell(s) to a variety of experiments can be performed quickly and cheaply in simulation. Simulated experiments may be performed to develop an understanding of the interrelationships of various environmental and other factors on the development of the biological system and/or on the biological system's effect on its environment. For example, simulated experiments may be performed to determine a set of environmental conditions that increases a growth rate of the biological system or that increases a rate of production of a substance of interest (e.g., an antibody, a hormone, a protein, an enzyme) by the biological system. Additionally or alternatively, the simulated experiments may be performed to develop an understanding of the effect of changes in the composition of the biological system (e.g., changes in the genetic or epigenetic makeup of the biological system) on the development or behavior of the biological system and/or to develop an understanding of the effect on changes in protein structure on the functionality of such proteins. For example, simulated experiments may be performed to determine a change in the genome of the biological system that increases a growth rate of the biological system and/or that increases a rate of production of a substance of interest by the biological system.

Biological systems are typically modeled using various equations or functions such as a system of differential equations and include many parameters, each corresponding to (e.g., 'modeling') an aspect of the structure and/or function of a biological system. For example, a parameter of a model could correspond to an amount and/or number of discrete instances of a constituent (e.g., a protein, a particular sequence of RNA, a metabolite, an ion, etc.) in the biological system, intrinsic rates, kinetic constants, concentrations of external metabolites, compartment sizes, a reaction rate of an enzyme, an affinity of an enzyme for a substrate or cofactor, a relationship between a DNA or RNA sequence and the function or properties of a related protein, a pH-dependence of the function of an enzyme or membrane protein, or some other properties of elements of the biological system. The structure of the model in terms of the mathematical representation of the function (e.g. deterministic, stochastic, logical or stoichiometric, etc.) which describes the system components and relationships is typically defined according to current knowledge, sometimes in combination with data-driven network inference techniques that aim to learn the likely structure of a system from observations of its variables. However, it is also necessary to obtain values for the parameters, from scientific literature and knowledge summarized in databases, experimentally determined values, or by using statistical approaches to estimate (or infer) these values by fitting model simulations to observed data Parameter estimation is the process of obtaining values for some or all parameters in a model from data (e.g., scientific literature, experimental measurements, or statistical estimates of values). Conducting physical experiments on a biological system is one technique for obtaining values of particular model parameters of interest for in silico models of the biological system. The utility of the models may be related to how accurately the models are able to predict the behavior of the biological system in physical experiments. Due to the complex dependencies of many different parameters that constitute the models, it may be difficult to create models to predict accurately the behavior of the biological system, e.g., based on newly collected experimental data. For example, biochemical reaction rates depend on numerous environmental (e.g. temperature, acidity, ionic strengths) and cellular (e.g. viscosity, allosteric regulation) factors. While physical experiments may be designed so that measurements of values within the biological system are as relevant as possible, few biological parameters can be measured directly in their appropriate in vivo context, from in vitro assays, or from other (related) species.

There are various reasons to be cautious of measurements obtained from physical experiments, for example, (i) thermodynamic and ecological differences between physical experiments may lead to pronounced differences in measured values; and (ii) growth characteristics of the biological system such as passage number, growth phase, and population doubling number can all have a significant impact on measured values. Additionally, not all relevant parameters may be known (even when data is included from related species) and, in some cases, may not be experimentally accessible or measurable. A key advantage of modelling a biological system is that it enables exploration of the influence of processes that may not be directly observed, by linking these processes in a mathematical framework to variables that may be probed experimentally. However, if the models are restricted to include only parameters that are experimentally accessible or measurable, then there is a risk of biasing the models (and thus experimental conclusions) according to the current experimental limitations. Accordingly, while substantial experimental data about biological systems already exists, additional robust and reliable experimental data would enable models that are more accurate. In particular, there is a need for expanding current experimental limitations with scalable techniques to quantify values for parameters consistently and simulate large models such as whole cell models accurately.

SUMMARY

In various embodiments, a system is provided for that comprises: one or more data processors; and a non-transitory computer readable storage medium containing instructions which, when executed on the one or more data processors, cause the one or more data processors to perform actions. The actions include: obtaining measurement data for one or more characteristics of a biological system developed in a culture system, where the measurement data is indicative of each of the one or more characteristics at a physiological steady state where growth of the biological system is occurring at a substantially constant growth rate; determining a value for a parameter of a model of the biological system based on an growth formula, the measurement data, and the substantially constant growth rate, where the model predicts a response of the biological system to a set of conditions based on a plurality of parameters including the parameter, and the parameter models an aspect of structure or function of the biological system; and parametrizing the model with at least the value determined for the parameter.

In some embodiments, the actions further include: prior to determining the value for the parameter, analyzing the model of the biological system to identify the parameter as having an unknown value and as being tied to a module used to model one or more biological processes of the biological system; and determining the one or more characteristics of the biological system that are associated with the identified parameter and are measurable in the culture system. Optionally, the parameterizing the model comprises: (i) identifying, for the module, one or more simulation parameters including the parameter, (ii) inputting the value for the parameter into the model, and (iii) fixing the value for the parameter across time-step iterations.

In some embodiments, the actions further include running a simulation assigned to the module of the model using an input data set and at least the value determined for the parameter to simulate at least a portion of the model of the biological system.

In some embodiments, the actions further include determining, for the culture system, a dilution cycle with a predetermined period and a desired optical density; measuring, for the dilution cycle, an actual optical density of a culture chamber of the culture system; determining, for the culture chamber, a dilution rate as a function between the desired optical density and the actual optical density; controlling a pump, a valve, or a combination thereof to provide fresh medium to the culture chamber at the dilution rate to return a turbidity of the biological system to the desired optical density; and measuring, by an analyzer, a characteristic of the one or more characteristics in a sample of the biological system from the culture chamber to obtain at least a portion of the measurement data. The obtaining the measurement data comprises retrieving the portion of the measurement data from the analyzer In some embodiments, the culture system is a turbidostat, and the one or more characteristics are measured after at least one dilution cycle with a period of at least 10 cell doublings.

In some embodiments, the actions further include: determining the substantially constant growth rate based on a growth curve of the biological system plotted using optical density measurements of the culture system across time; and generating the growth formula to scale at a same rate as the substantially constant growth rate, which allows for the value of the parameter to be determined without a time component or a relaxation time.

In some embodiments, the measurement data is obtain from a same sample of the biological system developed in the culture system, the measurement data includes the optical density measurements of the culture system, and the one or more characteristics include cell composition.

In some embodiments, the one or more characteristics include: (i) the substantially constant growth rate, and (ii) at least one of the following: RNA sequencing, total cellular protein, total cellular RNA, total cellular DNA, and dry cell weight.

In various embodiments, a computer-implemented method is provided for that comprises: obtaining measurement data for one or more characteristics of a biological system developed in a culture system, where the measurement data is indicative of each of the one or more characteristics at a physiological steady state where growth of the biological system is occurring at a substantially constant growth rate; determining a value for a parameter of a model of the biological system based on an growth formula, the measurement data, and the substantially constant growth rate, where the model predicts a response of the biological system to a set of conditions based on a plurality of parameters including the parameter, and the parameter models an aspect of structure or function of the biological system; and parametrizing the model with at least the value determined for the parameter.

In some embodiments, the method further comprises: prior to determining the value for the parameter, analyzing the model of the biological system to identify the parameter as having an unknown value and as being tied to a module used to model one or more biological processes of the biological system; and determining the one or more characteristics of the biological system that are associated with the identified parameter and are measurable in the culture system. Optionally, the parameterizing the model comprises: (i) identifying, for the module, one or more simulation parameters including the parameter, (ii) inputting the value for the parameter into the model, and (iii) fixing the value for the parameter across time-step iterations.

In some embodiments, the method further comprises running a simulation assigned to the module of the model using an input data set and at least the value determined for the parameter to simulate at least a portion of the model of the biological system.

In some embodiments, the method further comprises determining, for the culture system, a dilution cycle with a predetermined period and a desired optical density; measuring, for the dilution cycle, an actual optical density of a culture chamber of the culture system; determining, for the culture chamber, a dilution rate as a function between the desired optical density and the actual optical density; controlling a pump, a valve, or a combination thereof to provide fresh medium to the culture chamber at the dilution rate to return a turbidity of the biological system to the desired optical density; and measuring, by an analyzer, a characteristic of the one or more characteristics in a sample of the biological system from the culture chamber to obtain at least a portion of the measurement data. The obtaining the measurement data comprises retrieving the portion of the measurement data from the analyzer.

In some embodiments, the culture system is a turbidostat, and the one or more characteristics are measured after at least one dilution cycle with a period of at least 10 cell doublings.

In some embodiments, the method further comprises: determining the substantially constant growth rate based on a growth curve of the biological system plotted using optical density measurements of the culture system across time; and generating the growth formula to scale at a same rate as the substantially constant growth rate, which allows for the value of the parameter to be determined without a time component or a relaxation time.

In some embodiments, the measurement data is obtain from a same sample of the biological system developed in the culture system, the measurement data includes the optical density measurements of the culture system, and the one or more characteristics include cell composition.

In some embodiments, the one or more characteristics include: (i) the substantially constant growth rate, and (ii) at least one of the following: RNA sequencing, total cellular protein, total cellular RNA, total cellular DNA, and dry cell weight.

In various embodiments, a computer-program product is provided tangibly embodied in a non-transitory machine-readable storage medium, including instructions configured to cause one or more data processors to perform actions including: obtaining measurement data for one or more characteristics of a biological system developed in a culture system, where the measurement data is indicative of each of the one or more characteristics at a physiological steady state where growth of the biological system is occurring at a substantially constant growth rate; determining a value for a parameter of a model of the biological system based on an growth formula, the measurement data, and the substantially constant growth rate, where the model predicts a response of the biological system to a set of conditions based on a plurality of parameters including the parameter, and the parameter models an aspect of structure or function of the biological system; and parametrizing the model with at least the value determined for the parameter.

In some embodiments, the actions further include: prior to determining the value for the parameter, analyzing the model of the biological system to identify the parameter as having an unknown value and as being tied to a module used to model one or more biological processes of the biological system; and determining the one or more characteristics of the biological system that are associated with the identified parameter and are measurable in the culture system. Optionally, the parameterizing the model comprises: (i) identifying, for the module, one or more simulation parameters including the parameter, (ii) inputting the value for the parameter into the model, and (iii) fixing the value for the parameter across time-step iterations.

In some embodiments, the actions further include running a simulation assigned to the module of the model using an input data set and at least the value determined for the parameter to simulate at least a portion of the model of the biological system.

In some embodiments, the actions further include determining, for the culture system, a dilution cycle with a predetermined period and a desired optical density; measuring, for the dilution cycle, an actual optical density of a culture chamber of the culture system; determining, for the culture chamber, a dilution rate as a function between the desired optical density and the actual optical density; controlling a pump, a valve, or a combination thereof to provide fresh medium to the culture chamber at the dilution rate to return a turbidity of the biological system to the desired optical density; and measuring, by an analyzer, a characteristic of the one or more characteristics in a sample of the biological system from the culture chamber to obtain at least a portion of the measurement data. The obtaining the measurement data comprises retrieving the portion of the measurement data from the analyzer In some embodiments, the culture system is a turbidostat, and the one or more characteristics are measured after at least one dilution cycle with a period of at least 10 cell doublings.

In some embodiments, the actions further include: determining the substantially constant growth rate based on a growth curve of the biological system plotted using optical density measurements of the culture system across time; and generating the growth formula to scale at a same rate as the substantially constant growth rate, which allows for the value of the parameter to be determined without a time component or a relaxation time.

In some embodiments, the measurement data is obtain from a same sample of the biological system developed in the culture system, the measurement data includes the optical density measurements of the culture system, and the one or more characteristics include cell composition.

In some embodiments, the one or more characteristics include: (i) the substantially constant growth rate, and (ii) at least one of the following: RNA sequencing, total cellular protein, total cellular RNA, total cellular DNA, and dry cell weight.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTION OF THE DRAWINGS

The present invention will be better understood in view of the following non-limiting figures, in which.

Figure 1:
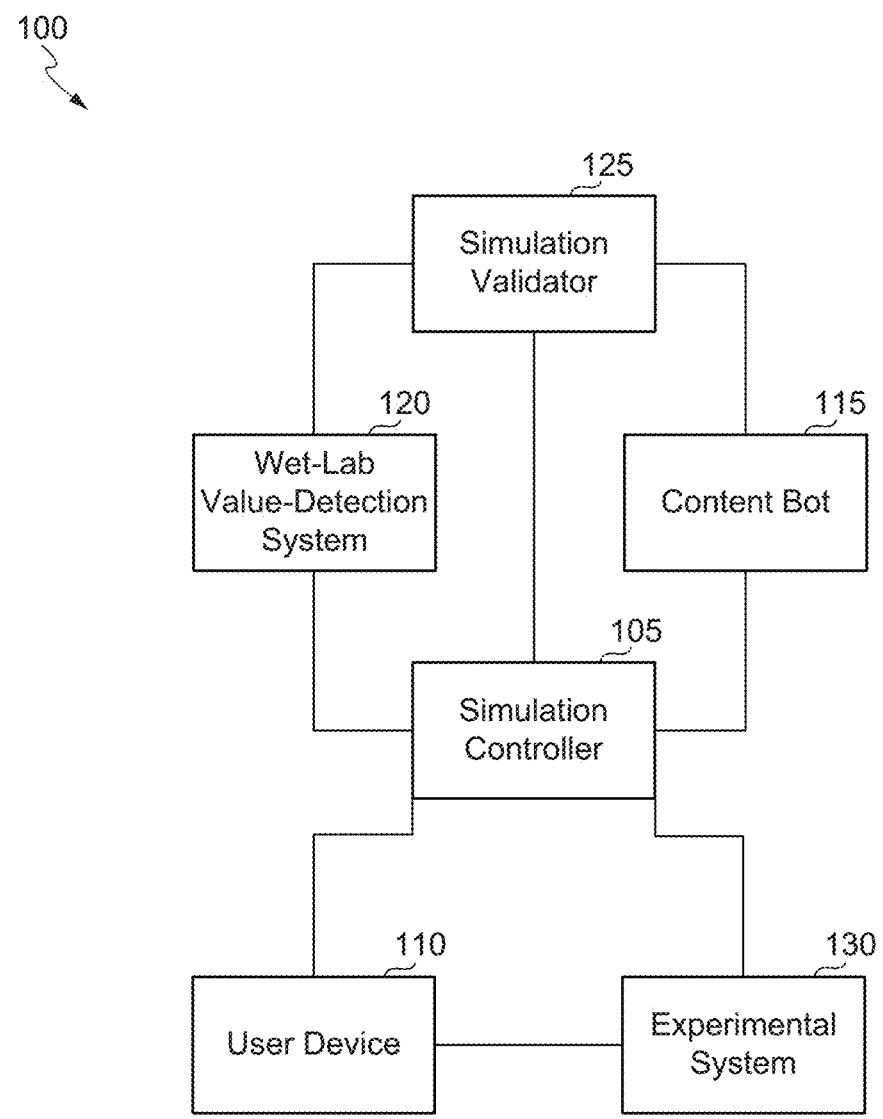
FIG. 1 shows an interaction system for configuring and using a simulation to facilitate subsequent experiment configurations according to various embodiments.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart or diagram may describe the operations as a sequential process, many of the operations may be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination may correspond to a return of the function to the calling function or the main function.

I. Introduction

The following disclosure describes a scalable experimental workflow for parameter estimation, and in particular to a scalable experimental workflow that uses a culture system to maintain a steady state in a biological system, and techniques for identifying values for parameters in a in silico model based on experimental data obtained from the biological system. In various embodiments, a parameter of a model (i.e., an in silico model) is identified that has an unknown value for modeling an aspect of structure or function of a biological system. For example, a parameter of the model could correspond to an amount and/or number of discrete instances of a constituent (e.g., a protein, a particular sequence of RNA, a metabolite, an ion, etc.) in the biological system, intrinsic rates, kinetic constants, concentrations of external metabolites, compartment sizes, a reaction rate of an enzyme, an affinity of an enzyme for a substrate or cofactor, a relationship between a DNA or RNA sequence and the function or properties of a related protein, a pH-dependence of the function of an enzyme or membrane protein, or some other properties of elements of the biological system. The value of the identified parameter could then be determined experimentally, and the model of the biological system updated to reflect the experimentally determined value of the identified parameter. By iterating this process (e.g., by repeating the process of identifying a parameter with an unknown value, experimentally evaluating the identified parameter, and updating the model to match the evaluation of the identified parameter), an accurate model of the biological system may be generated.

A fundamental challenge to the modeling of a biological system such as whole cell is integrating the behavior of individual species and reactions to the cellular level over several spatial and temporal scales. This is challenging because it requires accurate parameter values and scalable methods for simulating large models. To overcome this fundamental challenge requires assembling comprehensive data about every molecular species and molecular interaction. This is especially difficult because not all relevant parameters may be known, e.g., in some cases, may not be experimentally accessible or measurable, and where data is experimentally accessible or measurable, the data is not always reliable or introduces an implicit bias into the parameter estimation. For example, conventionally, characterization of biological systems has been carried out using batch culture methods. However, in batch culture, the chemical environment is continually changing as cells grow, divide, consume nutrients, and excrete waste products. These changes associated with growth have substantial effects on cellular physiology and engineered biological components, which can in turn cause the mischaracterization of a system's input-output response or require the consideration of uncontrolled disturbances to the system.

To address these limitations and problems, experimental workflow and modeling techniques of various embodiments disclosed herein enable experimental measurements to be taken at a physiological steady state where growth of a biological system is occurring at a substantially constant growth rate, and the physiological steady state allows for data from the experimental measurements to be scaled and used to parameterize an in silico model of the biological system. One illustrative embodiment of the present disclosure is directed to a system that includes one or more data processors and a non-transitory computer readable storage medium containing instructions which, when executed on the one or more data processors, cause the one or more data processors to perform actions including: analyzing a model of a biological system to identify a parameter, where the model predicts a response of the biological system to a set of conditions based on a plurality of parameters including the identified parameter, and the identified parameter models an aspect of structure or function of the biological system; determining one or more characteristics of the biological system that are associated with the identified parameter and are measurable in a culture system; obtaining measurement data for the one or more characteristics of the biological system developed in the culture system, where the measurement data is indicative of each of the one or more characteristics at a physiological steady state where growth of the biological system is occurring at a substantially constant growth rate; determining a value for the identified parameter based on an growth formula, the measurement data, and the substantially constant growth rate; and parametrizing the model with at least the value determined for the identified parameter.

As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 5, and 10 percent. As used herein, when an action is "based on" something, this means the action is based at least in part on at least a part of the something.

Advantageously, these approaches provide a scalable experimental workflow for parameter estimation. More specifically, these approaches maintain a stable environment in which a biological system is developing which benefits characterization of the in silico model of the biological system. This solution is scalable to estimate one or more parameters of the model from related measurement data indicative of characteristics of the biological system in the stable environment, and thus enabling parameterization of larger models such as whole cell models. Furthermore the measurement data obtained from the stable environment is robust, reliable, and more readily able to estimate values for parameters consistently.

II. Interaction System and Biological System Modeling Techniques

FIG. 1 shows an interaction system 100 for configuring instances or versions of a model and using a simulation to facilitate subsequent experiment configurations (e.g., simulation of a biological system's response to a new demand) according to various embodiments. Each instance of the models may have a combination of modules, perturbations (such as knockouts), and may be built using a particular set of experimental data. In order to facilitate the configuring of a model (e.g., a biological system) and simulate an outcome of the model, the interaction system 100 can include one or more components, each of which can include (for example) one or more servers, one or more computers and/or one or more mobile devices. In some instances, two or more of the components can be included in a same server, same server system, same computer, etc. Interaction system 100 can include one or more networks (e.g., a wired network, a wireless network, the Internet, a local area network, a wide area network, a short-range network, etc.), such that each component in the interaction system 100 can communicate with one or more other components in the interaction system 100.

Interaction system 100 can include a simulation controller 105 that defines, generates, updates and/or executes each of one or more simulations. A simulation can be configured to simulate dynamic progression through states, a time-evolved state of a model of a biological system and/or a steady state based on an iterative module-based assessment. It will be appreciated that identifying a steady-state and/or balanced solution for a module at a given time step need not indicate that a steady-state and/or balanced solution has been, can be or will be identified for the model in general (e.g., as metabolites produced and/or consumed at one module may further be produced and/or consumed at another module that need not be configured for balancing fluxes).

A given model can be used to generate and run any number of simulations. Differing initial conditions and/or differing automatically generated values in stochastic portions of the simulation (e.g., generated using a pseudo-random number generation technique, a stochastic pull from a distribution, etc.) can result in different output results of different simulations. The biological system model can be made up of one or more modules, and during a simulation run, each module is run independently and passes results back up to the biological system model level. More specifically, the biological system (e.g., a whole cell) may be modeled in accordance with a coordinated operation of multiple modules that represent structure(s) and/or function(s) of the biological system. Each module may be defined to execute independently, except that a shared set of state values (e.g., a state vector) maintained at the biological system model level may be used and accessed by multiple modules at each time point.

In some instances, each module of the biological system is configured to advance across iterations (e.g., time points) using one or more physiological and/or physics-based models (e.g., flux balance analysis (FBA), template synthesis, bulk-mass flow analysis, constant non-specific degradation, empirical analysis, etc.). The module-specific iteration processing can further be based on one or more module-specific state values (as determined based on an initial definition for an initial iteration processing or a result of a previous iteration processing for a subsequent iteration processing). The module-specific iteration processing can further be based on one or more parameters defined for the module that are fixed and/or static across iterations across iterations.

Simulation controller 105 can generate simulation configurations using one or more inputs received from a user device 110. For example, simulation controller 105 may generate an interface (or may at least partly define specifications for an interface) that is to be availed and/or transmitted to user device 110 and to include input fields configured to receive inputs that correspond to a selection of (for example) one or more modules to be used for a given biological system model, a model type to be used for each of the one or more modules, one or more parameters that are to be effected by a given module's model and used during execution, and/or one or more initial state-value definitions that are to be used by a given module's model and used during execution. In some instances, the interface identifies a default value for each of one, more or all parameters of the model and for each of one, more or all of the initial-state values of the model and is configured to receive a modification to a subset or all of the parameters and/or initial-state values for which a default value was identified. In some instances, modifying a default initial-state value and/or parameter can correspond to a perturbation of performance of a corresponding module and/or the biological system.

Figure 2:
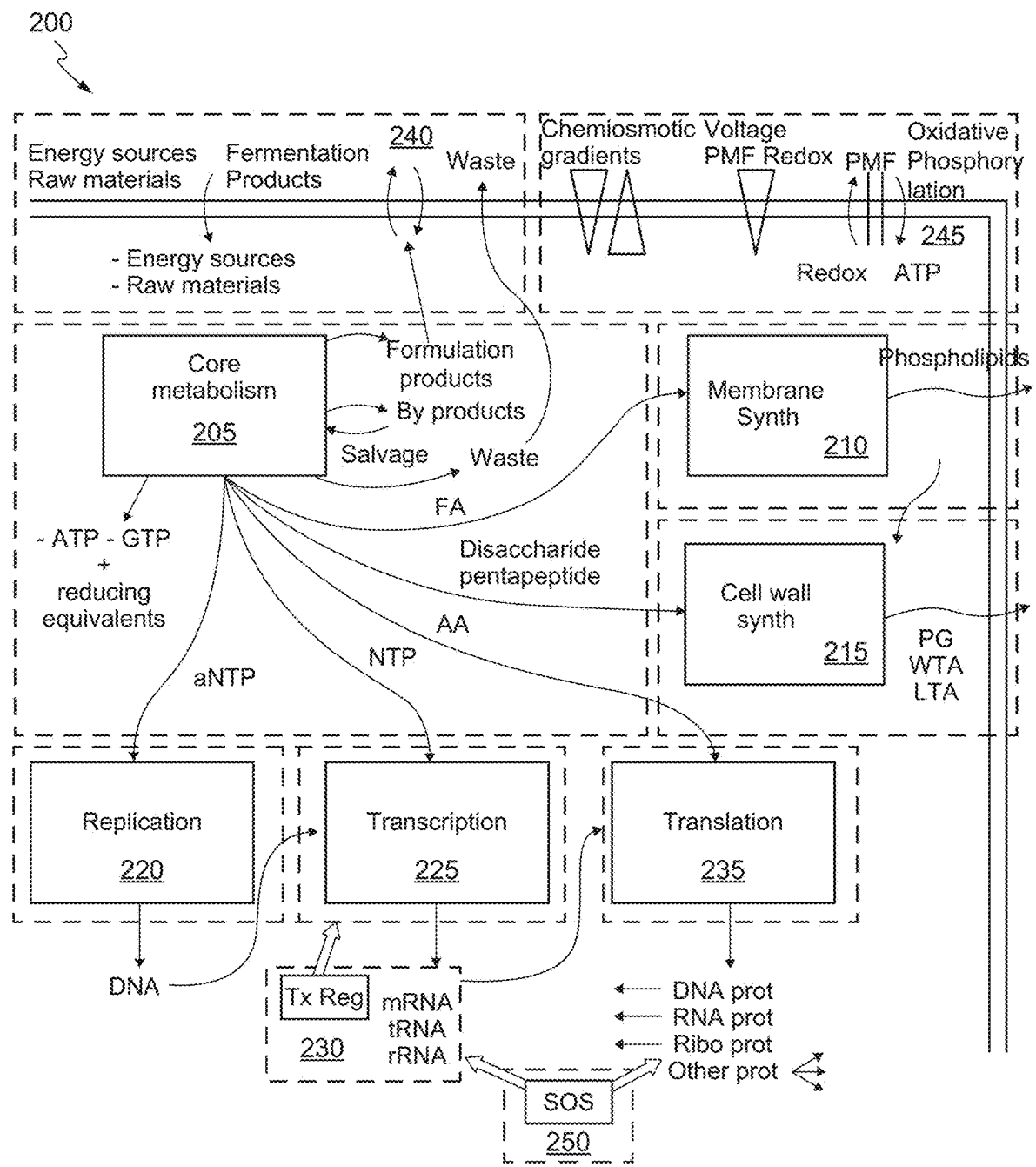
FIG. 2 shows a representation of modules representing distinct biological functions according to various embodiments.

As another example, the interface may further or alternatively be configured to receive an input that corresponds to a selection of one or more default modules and a selection of a model type to be used for each of one or more modules. For example, the interface may include one or more modules (as shown in FIG. 2) representing distinct biological functions in a biological system model, and for each module: a name of the module, a default model type for the module and an option configured to receive a selection of another model type for the module (e.g., that identifies one or more other model types that can be selected for the module).

Default structure of a simulation (e.g., corresponding to default modules, default parameters, default initial-state values and/or default model selections) can be determined based on detected internal or external content and/or based on lab results (e.g., results from physical experiments). The content can include (for example) online, remote and/or local content that is collected by a content bot 115. Content bot 115 can (for example) include a crawler that performs a focused crawling and/or focused browsing (for example) the Internet, a part of the Internet, one or more pre-identified websites, a remote (e.g., cloud-based) storage system, a part of a remote storage system, a local storage system and/or a part of a local storage system. The crawling can be performed in accordance with one or more crawling policies and/or one or more queries that corresponds to one or more modules and/or models (e.g., where each query includes a variable name, representation or description and/or a cellular-function name, representation or description).

The lab results can be received from a wet-lab value detection system 120, which can be configured to trigger performance of one or more investigations (e.g., physical experiments) to detect and/or measure data corresponding to an initial-state value and/or data corresponding to a characteristic or parameter of a biological system. Wet-lab value-detection system 120 can transmit one or more results of the investigation(s) back to simulation controller 105, which may thereafter determine and/or define a default initial-state value or parameter or a possible modification thereof based on the result(s).

Interaction system 100 further includes a simulation validator 125, which can be configured to validate performance of a simulation. The validation may be performed based on pre-identified indications as to how a biological system functions normally and/or given one or more perturbations. Such indications can be defined based on content collected from content bot 115 and/or results from wet-lab value-detection system 120. The data used to validate the simulation may include (for example) one or more balanced values, one or more values indicative of cell dynamics, one or more steady-state values, one or more intermediate values and/or one or more time-course statistics. Simulation validator 125 may return a performance result that includes (for example) a number, category, cluster or binary indicator to simulation controller 105. Simulation controller 105 may use the result to determine (for example) whether a given simulation configuration is suitable for use (e.g., in which case it may be selectable in an interface).

After a simulation is configured with definitions and/or selections of modules, module-specific models, parameters and/or initial-state values, simulation controller 105 can execute the simulation (e.g., in response to receiving an instruction from user device 110 to execute the simulation). The simulation execution can produce one or more simulation results, which may include (for example) one or more balanced values, kinetic values, etc. For example, the simulation can identify a solution for a set of reaction-corresponding stoichiometric equations using linear algebra, such that production and consumption of metabolites represented in the equations is balanced. Notably, this balance may be specific to a given module and need not be achieved for all metabolites produced or consumed by reactions for a given module (e.g., as a non-zero net production or consumption of one or more boundary metabolites may be pre-defined and/or a target result for a module). Simulation controller 105 can transmit the results (e.g., via an interface) to user device 110.

In some instances, the results can be used to trigger and/or define a subsequent experiment. For example, simulation controller 105 may determine whether a given predefined condition is satisfied based on the results and, if so, may transmit simulation-specific data (e.g., indicating one or more initial-state values, parameters, mutations corresponding to simulation definitions, etc.) to an experimental system 130. The transmission may be indicative of and/or include an instruction to perform an experiment that corresponds to the simulation.

As another example, upon receiving simulation results from simulation controller 105, user device 110 can present an interface that includes some or all of the results and an input component configured to receive input corresponding to an instruction to perform an experiment that corresponds to the simulation. Upon receiving a selection at the input component, user device 110 may transmit data corresponding to the simulation to experimental system 130. After performing a requested experiment, experimental system 130 may return one or more results to simulation controller 105 and/or user device 110.

FIG. 2 shows an illustrative representation of given biological system model 200. The overall modeling strategy includes partitioning the biological system model 200 into modules that can be modeled separately, using a methodology and level of detail appropriate to and/or selected for each module. The partitioning and level of detail for each module can be selected based on (for example) the experiments or simulations that are to be run by the model (e.g., the questions trying to be solved by the model). The selection may be made by the modeler and/or computing system (e.g., the interaction system 100 described with respect to FIG. 1). For example, a user working through an interface of an integrated development environment, a script, and/or an automated system may be implemented to select one or more modules and select a model type to be used for each of one or more modules to ultimately generate the biological system model 200. Additionally or alternatively, the partitioning can be customized and depend on an assessment of the biological functions defined for the initial high-level data set. For example, a separate module may be defined to represent each of the following biological functions: core metabolism 205, membrane synthesis 210, cell-wall synthesis 215, DNA replication 220, transcription 225, transcription regulation 230, translation 235, RNA salvage (not shown), protein and RNA maturation, protein salvage (not shown), transmembrane transport 240 (including electron chain, oxidative phosphorylation, redox, and pH interconversion activity 245), signal transduction (not shown), stress response and growth rate regulation 250, cell division, chemotaxis (not shown), and cell-cell signaling (not shown).

Biological system model 200 can include at least one module that handles core metabolism 205. One possible core metabolic module uses an FBA model, which takes its general shape from standalone FBA, but includes modifications that account for interactions of the core metabolic module with other modules. Each of one, more or all other modules may have their own production and consumption of some of the same molecules within the FBA network, as described in further detail herein. However, as should be understood to those of ordinary skill in the art, an FBA model does not have to be incorporated into the overall biological system model 200 in order for every simulation to work. Instead, various types of models can be used for the modules (e.g., core metabolism 205, membrane synthesis 210, cell-wall synthesis 215, etc.) so long as the type of models can be configured to read values from the state vector and return a list of changes that should be made to the state vector.

For one exemplary instantiation of biological system model 200, core metabolism 205, membrane synthesis 210, and cell-wall synthesis 215 may be encompassed as a single FBA problem, whereas DNA replication 220, transcription 225, transcription regulation 230, and translation 235 may be isolated from the rest of the metabolic network. Meanwhile, transcription 225 and translation 235 may use a template synthesis model, and DNA replication 220 may use a bulk mass-flow model. Transcription regulation 230 may be empirical and static. Optionally, RNA salvage may be modeled using constant non-specific degradation, polymerized DNA, RNA, and protein levels may be determined by the intrinsic rates of the processes that produce them, and the remainder of the components are provided as inputs or parameters of the model.

For another exemplary instantiation of biological system model 200, core metabolism 205 may be encompassed as a single FBA problem. The balance of internal metabolite pools and the supply of building blocks for other processes may be maintained by core metabolism 205. DNA replication 220, transcription 225, transcription regulation 230, and translation 235 may then be isolated from the rest of the metabolic network. Membrane biosynthesis 210 and cell-wall synthesis 215 may be modeled by substrate- and catalyst-driven kinetics. Import and export rates and all exchange with the environment may be driven by the kinetics of membrane transport. Transcription 225 and translation 235 may use a template synthesis model, and DNA replication 220 may use a bulk mass-flow model. Transcription regulation 230 may be empirical and static. Optionally, RNA salvage may be modeled using representations of constant non-specific degradation, while polymerized DNA, RNA, and protein levels may be determined by the intrinsic rates of the processes that produce them, and the remainder of the components for the biological system can be provided as inputs or parameters of the model.

For another exemplary instantiation of biological system model 200, core metabolism 205 may be encompassed as an FBA problem, whereas one or more of membrane synthesis 210, cell-wall synthesis 215, DNA replication 220, transcription 225, transcription regulation 230, and translation 235 can be isolated from the rest of the metabolic network. The balance of internal metabolite pools and the supply of building blocks for other processes may be maintained by core metabolism 205. Membrane biosynthesis 210 and cell-wall synthesis 215 may be modeled by substrate and catalyst driven kinetics. Import and export rates, and all exchange with the environment may be driven by the kinetics of membrane transport. Redox balance, pH, and chemiosmotic gradients may be maintained explicitly. DNA replication 220, transcription 225 and translation 235 may use models based on initiation, elongation, and termination, Transcription regulation 230 may be pattern driven. Stress response and growth rate regulation 250 may be modeled using feedback control mechanisms. Optionally, RNA salvage may be modeled using constant non-specific degradation, while polymerized DNA, RNA, and protein levels may be determined by the intrinsic rates of the processes that produce them, and the remainder of the components for the biological system can be provided as inputs or parameters of the model.

While the biological system model 200 has been described at some length and with some particularity with respect to several described modules, combinations of modules, and simulation techniques, it is not intended that the biological system model 200 be limited to any such particular module configuration or particular embodiment. Instead, it should be understood that the described embodiments are provided as examples of modules, combinations of modules, and simulation techniques, and the modules, combinations of modules, and simulation techniques are to be construed with the broadest sense to include variations of modules, combinations of modules, and simulation techniques listed above, as well as other modules, combinations of modules, and simulation techniques configurations that could be constructed using a methodology and level of detail appropriate to each module and the biological system model 200.

Figure 3:
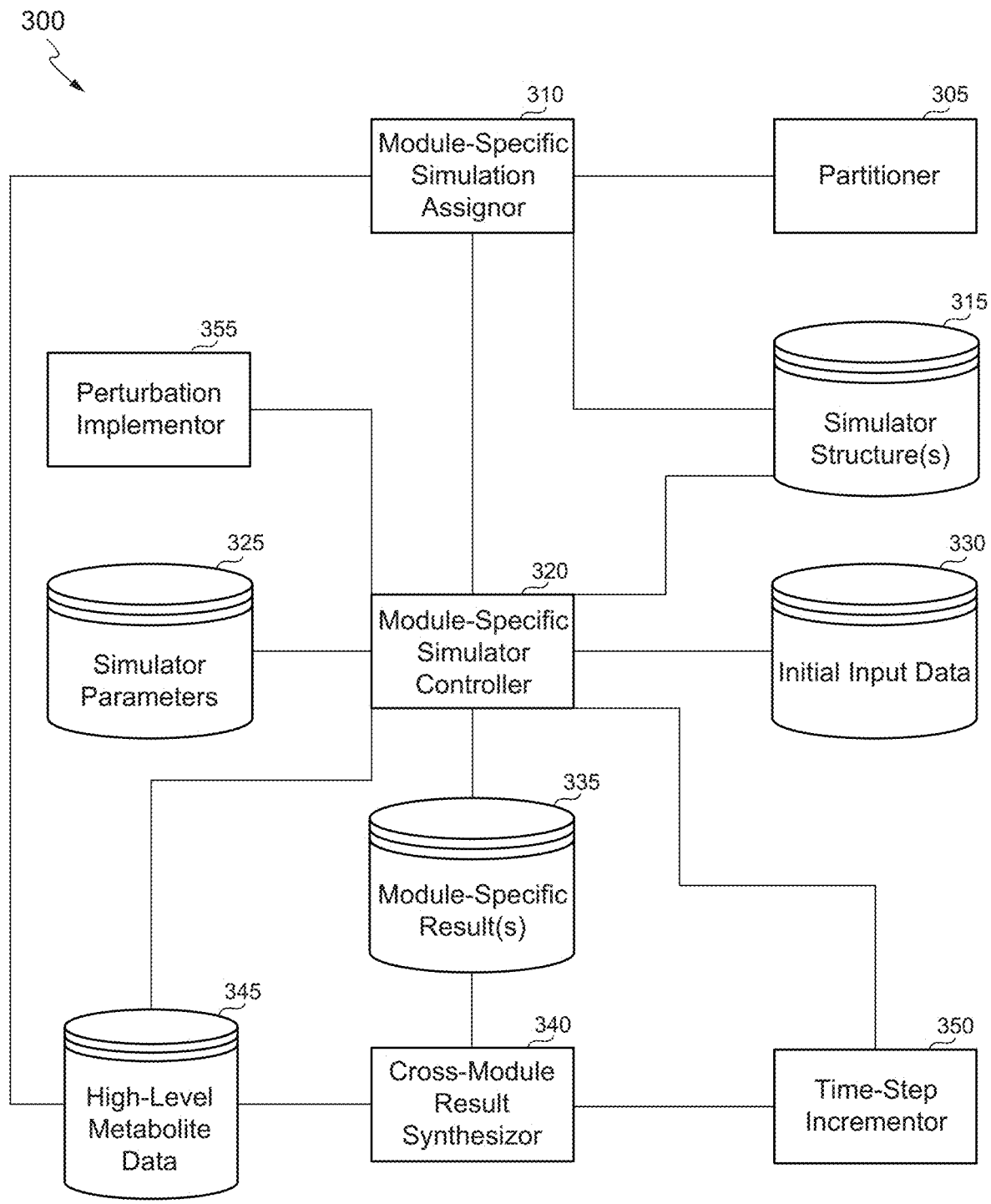
FIG. 3 shows a simulation controller that dynamically integrates results generated by different types of models to simulate higher-level states and reactions according to various embodiments.

FIG. 3 shows a simulation controller 300 that dynamically integrates results generated by different types of models configured by an integrated development environment (e.g., the interaction system 100 described with respect to FIG. 1) to simulate higher-level states and reactions of a biological system model (e.g., biological system model 200 as described with respect to FIG. 2) according to various embodiments. A partitioner 305 that can identify one or more modules to potentially use for a simulation. In some instances, the modules are identified to correspond to distinct biological functions or physiological processes within a biological system model. Nonetheless, at least one module (e.g., a core module) may address in more detail or cover a larger set of biological functions (e.g., correspond to a core level of physiology across the biological system such as general metabolism of the biological system), whereas at least one other module (e.g., a non-core module) may address in less detail or cover a smaller set biological function (e.g., correspond to transcription and/or translation).

A module-specific simulation assignor 310 may assign, to each module, a simulation type. The simulation type can be selected from amongst one or more types that are associated with the module and/or corresponding physiological process. The one or more types may differ with regard to (for example) a degree of detail to which a physiological process is modeled and/or how the process is modeled. For example, the one or more types may include a simulation using a metabolism-integrated model (e.g., in which specific end products are added to an objective function of a metabolism-based model), substrate- and/or catalyst-drive model using kinetic parameters and reactions, and/or higher-order structure model. A structure for each simulation type (e.g., that indicates how the simulation is to be performed and/or program code) is included in a simulator structure data store 315. Simulator structure data store 315 can further store an association between each simulation type and one or more modules for which the simulation type is associated and is permitted for selection for use.

A module-specific simulator controller 320 can identify, for each module, one or more simulation parameters and an input data set. The simulation parameters may be retrieved from a local data store (e.g., a simulator parameters data store 325) or from a remote source. Each of one or more of the simulation parameters may have been identified based on (for example) user input, a data-fitting technique and/or remote content. The parameter(s), once selected, may be fixed across time-step iterations.

At an initial time step, the input data set can include one or more initial input values, which may be retrieved from a local data store (e.g., an initial input data store 330) or from a remote source. Each of one or more of the initial input values may have been identified based on (for example) user input, a data-fitting technique and/or remote content. With respect to each subsequent time step, the input data set can include (for example) one or more results from a previous iteration of the module and/or one or more high-level results (e.g., cumulative or integrated results) generated from a previous iteration of the multi-module simulation. For example, a module-specific results data store 335 may store each of one, more or all results generated by the assigned simulation for each of one, more or all past time steps, and at least one of the stored results associated with a preceding time step (e.g., most recent time step) can be retrieved.

Upon identifying the input data set and parameters, module-specific simulator controller 320 can run the simulation assigned to the module. Execution of module-specific simulations may be performed concurrently, in parallel and/or using different resources (e.g., different processors, different memory and/or different devices). Results of the simulation run can be stored in module-specific results data store 335.

After results have been generated for each module, a cross-module result synthesizor 340 can access the module-specific results (from one or more module-specific results data stores or direct data availing) and synthesize the results to update high-level data such as a state vector (e.g., stored in a high-level metabolite data store 345). For example, a set of results generated by different modules but relating to a same variable may be identified. The results may be integrated by (for example) summing variable changes as indicated across the results (e.g., potentially with the implementation of one or more caps pertaining to a summed change or to a value of a variable after the summed change is effected). In some instances, a hierarchy is used, such that a result from one module (if available or if another condition is met) is to be exclusively used and a result from another module is to otherwise be used.

Upon synthesizing the results, a time-step incrementor 350 can increment a time step to a next time step so long as the simulation has not completed. It may be determined that the simulation is complete when (for example) processing for a predefined number of time steps has been performed, a particular result is detected (e.g., indicating that a target cell growth has occurred or that a cell has died) or steady state has been reached (e.g., as indicated by values for one or more predefined types of results differing by less than a predefined threshold amount across time steps). When the time step is incremented, module-specific simulator controller 320 can, for each module, collect a new input data set and run the assigned simulation. When the simulation is complete, an output can be generated to include one or more module-specific results, some or all high-level data and/or processed versions thereof. For example, the output may include time-course data for each of one or more metabolites, growth of the biological system over a time period (e.g., as identified by a ratio of availability values of one or more particular metabolites at a final time step as compared to availability values at an initial time step) and/or a growth rate. The output can be transmitted to another device (e.g., to be presented using a browser or other application) and/or presented locally.

Multi-module simulation controller 300 can also include a perturbation implementor 355. Perturbation implementor 355 can facilitate presentation of an interface on a user device. The interface can identify various types of perturbations (e.g., mutations). Perturbation implementor 355 may facilitate the presentation by transmitting data (e.g., HTTP data) to a user device, such that the interface can be presented online. Perturbation implementor 355 can detect a selection that corresponds to a particular perturbation and can send an indication to module-specific simulator controller 320. Module-specific simulator controller 320 can use functional gene data to determine how the mutation affects one or more metabolites and/or one or more simulated processes. A structure of a simulator, one or more simulator parameters and/or one or more initial-input values may then be adjusted in accordance was the perturbation's effects. Thus, multi-module simulation controller 300 can generate output that is indicative of how the perturbation affects (for example) physiological processes and/or growth of the biological system.

Figure 4:
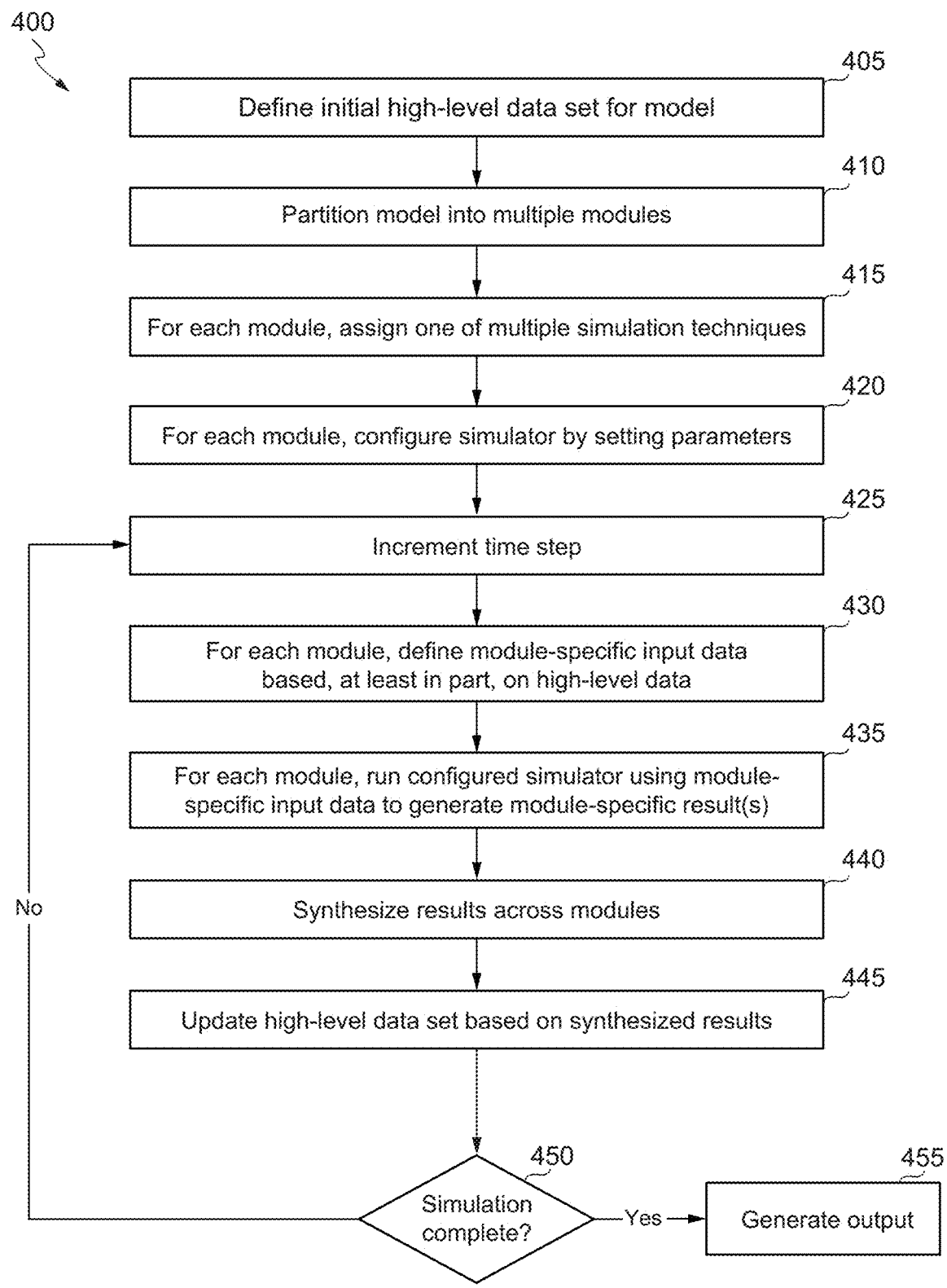
FIG. 4 shows a process for dynamically synthesizing results generated by multiple simulators to simulate higher-level results according to various embodiments.

FIG. 4 shows a process 400 for dynamically synthesizing results generated by multiple simulators to simulate higher-level results according to various embodiments. In some embodiments, the processes depicted in process 400 are implemented by the interaction system 100 of FIG. 1, and discussed with respect to the simulation controller 300 of FIG. 4. Process 400 begins at block 405 at which an initial high-level data set is defined for a biological system model. The initial high-level data set can identify (for example) variables, which may be referred to as the state of the biological system model or the state of the simulation, and these variables may be structured as a data structure (e.g., a state vector) and updated throughout a simulation run. In some instances, the variables include an initial availability of each of a set of molecules such as metabolites. The initial availability may be defined based on (for example) a default value, user input, data extracted from content (e.g., online content, remote content or local content that pertains to the molecules), etc. In some instances, the initial availability is determined based on whether any perturbation was identified (e.g., via user input) for a given simulation. If a perturbation was identified, the initial availability may be determined based on a particular perturbation that was identified and by using (for example) a look-up table to determine for which molecule(s) the perturbation affects an availability value and characteristics of such effect.

At block 410, a biological system model (e.g., a whole cell model) is partitioned into multiple modules. The partitioning can depend on metabolite dependencies and/or biological-functioning assessment. For example, a separate module may be defined to represent each of the following biological functions: core metabolism, membrane synthesis, cell-wall synthesis, DNA replication, transcription, transcription regulation, translation, RNA salvage, protein and RNA maturation, protein salvage, transmembrane transport (including electron chain, oxidative phosphorylation, redox, and pH interconversion activity), signal transduction, stress response and growth rate regulation (SOS), cell division, chemotaxis, and cell-cell signaling, as discussed in further detail with respect to FIG. 2. In some instances, two or more of these functions may be represented in a core module that models cell composition and growth using a single model. Particular cellular functioning need not be explicitly modeled and instead dynamics of end products of the particular cellular functioning may be modeled. For example, a core module may use a flux-based analysis or a simulation technique as described herein (e.g., in relation to FIG. 5 or FIG. 6).

In some instances, the partitioning may be performed based on user input and/or one or more default configurations. For example, an interface may be presented that identifies each potential separate module (e.g., an interface may be presented via simulation controller 105 as described with respect to FIG. 1). A default configuration may be to integrate the module into a core module (e.g., a core metabolism module) unless a contrary input is received or to perform a simulation using modeling specific to the module unless a contrary input is received. For example, an interface may be configured to receive one or more selections of modules that are to be excluded from a core module and to then integrate each other module into the core module.

At block 415, for each module, one or more simulation techniques are assigned to the module. A simulation technique may include a model type. In some instances, a simulation technique that is assigned to a core module includes a flux-based analysis or other simulation technique, as described herein. In some instances, a simulation technique includes a mechanistic model, a kinetic model, a partial kinetic model, a substrate- and/or catalyst-driven model, and/or a structural model. The simulation technique may be assigned based on (for example) user input and/or one or more predefined default selections. For example, for each non-core module, a default selection may be predefined that represents particular functioning of the module, and for each core module, a default selection may be predefined that simulates dynamics of metabolites across a simulated time period. An interface may identify, for each module, the default selection along with one or more other simulation techniques that are associated with the module (e.g., with the association(s) being based on stored data and/or a predefined configuration). User input may then indicate that an alternative simulation technique is to be used for one or more modules.

At block 420, for each module, a simulator is configured by setting parameters and variables. The parameters (e.g., numeric values) may correspond to inputs to be used in the simulation technique assigned to the module and that are not changed across time steps of the simulation. The particular parameters may be determined based on (for example) stored data, content, a communication from another system and/or user input. The one or more module-specific or cross-module variables (e.g., identifying an initial availability of one or more metabolites) may correspond to inputs to be used in the simulation technique assigned to the module and may be changed across time steps of the simulation. For example, a parameter may be determined for a simulator that sets a minimum viable pH in the cytoplasm (below which the cell dies), and a variable may be identified that describes a current pH in the cytoplasm. The variable (current pH) might change throughout the simulation; however, the parameter (the minimum possible pH) would not change and remains fixed. An initial value of the pH variable may be identified, e.g., the value at the start of the simulation may be set in step 405 or if it is module specific then it may be set in step 420, and like the minimum pH parameter this would be used as an input into the simulation. The values of variables and parameters are both inputs, but the distinction is that variables can change from their initial values, and parameters are fixed throughout the simulation run.

At block 425, a time step is incremented, which can initially begin a given simulation. At block 430, for each module, module-specific input data is defined at least in part on the high-level data. More specifically, a high-level data structure may identify, for each of a set of molecules (e.g., metabolites), an availability value. Each availability value may initially be set to an initial availability value, which may thereafter be updated based on processing results from each module that relates to the molecule. For a given module, at each time step, a current availability value can be retrieved from the data structure for each molecule that pertains to the simulation technique assigned to the module. The module-specific input data may further include one or more lower-level values that are independent from processing of any other module. For example, one or more variables may only pertain to processing of a given module, such that the module-specific input data may further include an initial value or past output value that particularly and exclusively relates to the module.

At block 435, for each module, the configured simulator assigned to the module is run using the module-specific input data to generate one or more module-specific results. The one or more module-specific results may include (for example) one or more updated molecule availability values and/or a change in one or more availability values relative to corresponding values in the input data.

At block 440, results can be synthesized across modules. The synthesis may include summing differences across modules. For example, if a first module's results indicate that an availability of a given molecule is to be increased by 5 units and a second module's results indicate that an availability of the given metabolite is to be decreased by 3 units, a net change may be calculated as being an increase in 2 units. The net change can then be added to a corresponding availability value for the molecule that was used for the processing associated with the current time step and returned as a list of changes that should be made to the state vector. One or more limits may be applied to a change (e.g., to disallow changes across time steps that exceed a predefined threshold) and/or to a value (e.g., to disallow negative availability values and instead set the value to zero).

At block 445, the high-level data set is updated based on the synthesized results. The update can include adding data to a data structure such as a state vector from which one or more modules retrieve high-level data. The added data can include the synthesized results in association with an identifier of a current time step. Thus, the data structure can retain data indicating how an availability of a metabolite changed over time steps. It will be appreciated that alternatively the update can include replacing current high-level data with the synthesized data.

At block 450, it is determined whether the simulation is complete. The determination may be based on a number of time steps assessed, a degree to which data (e.g., high-level data) is changing across time steps, a determination as to whether a steady state has been reached, whether one or more simulated biological events (e.g., cell division or cell death) have been detected, etc. If the simulation is not complete, process 400 returns to block 425.

If the simulation is complete, process 400 continues to block 455, at which an output is generated. The output may include some or all of the high-level data and/or some or all of the module-specific results. For example, the output may include final availability values that correspond to a set of metabolites and/or a time course that indicates a change in the availability of each of one or more metabolites over the simulated time period. The output may be presented at a local device and/or transmitted to another device (e.g., for presentation).

Figure 5:
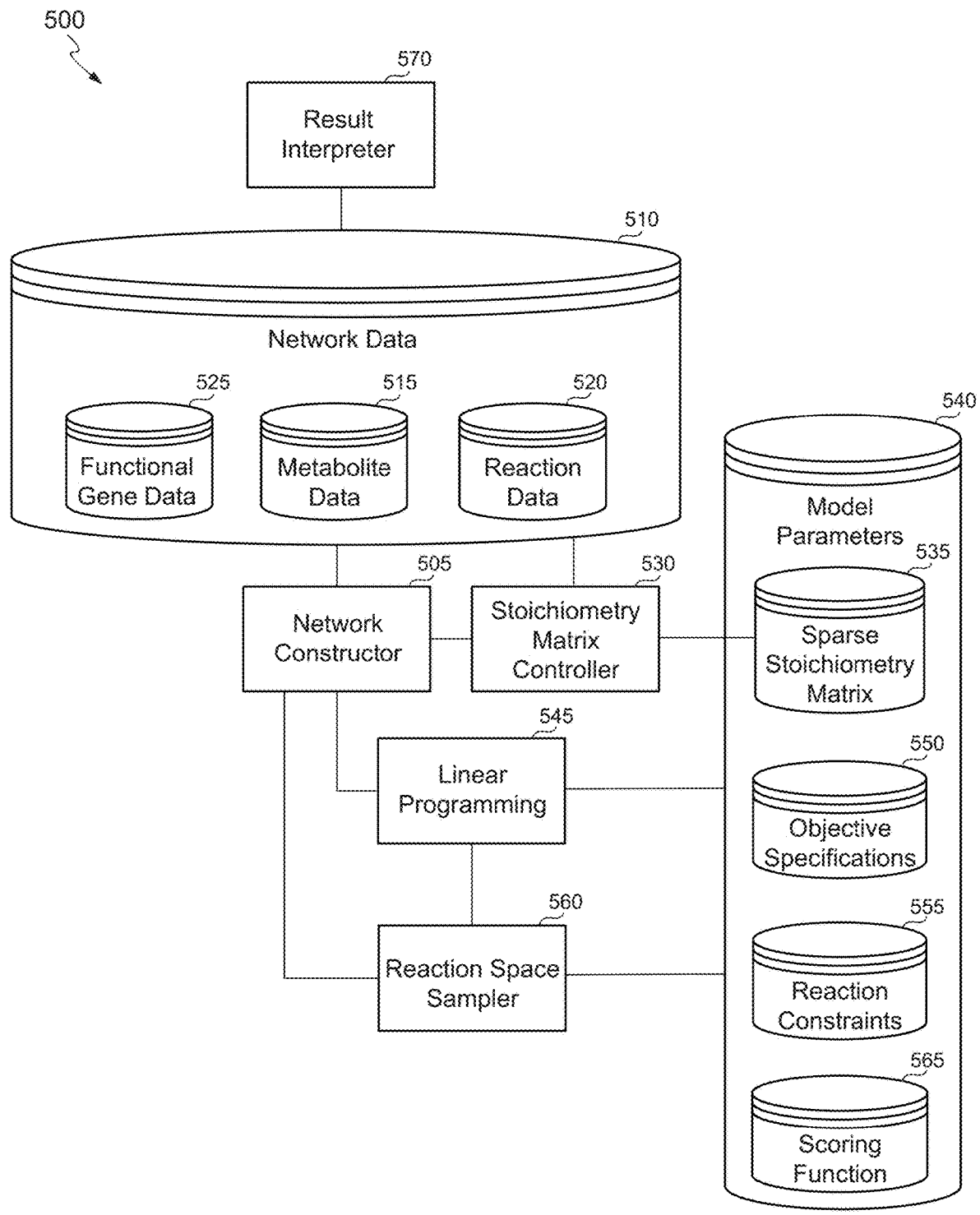
FIG. 5 shows a module-specific simulation controller to simulate states and reactions according to various embodiments.

FIG. 5 shows a module-specific simulation controller 200 to simulate states and reactions of modules configured by an integrated development environment (e.g., the interaction system 100 described with respect to FIG. 1) according to various embodiments. A network constructor 505 can be configured to use a model to simulate actions performed by a module of a biological system model (e.g., biological system model 200 as described with respect to FIG. 2). In some instances, the model is flux balance analysis, and/or the model is configured to solve for updated state values based on a set of equations that represent concentration changes in the network (e.g., a metabolic network). As should be understood by those of ordinary skill in the art, a biological system model such as a whole cell model does not have to include an FBA module. For example, from the framework described herein, biological processes such as core metabolism may be modeled that is completely different from FBA. In such an instance, part or all of the description and drawings pertaining to FIGS. 5 and 6 that is specific to FBA (e.g., objective functions, constraints, and linear programming) may not be relevant to that particular instantiation of the model or to simulations run with that model. However, many of the components and techniques described with respect to FIGS. 5 and 6 could be applied to simulate states and reactions of modules implemented by other models. For example, any module can read values from the state vector and return an indication of one or more changes that should be made to the state vector. The FBA module (if it's even present in a particular instantiation of the model) may read and return more values than any other model, but a module modeled with FBA need not be handled by the simulation controller 300 any differently from other modules and/or models described herein.

Network constructor 505 can access a set of network data (e.g., parameters and variables) stored in a network data store 510 to define the model. Metabolite data 515 can identify each metabolite of a metabolome. As used herein, a "metabolite" is any substance that is a product of metabolic action or that is involved in a metabolic process including (for example) each compound input into a metabolic reaction, each compound produced by a metabolic reaction, each enzyme associated with a metabolic reaction, and each cofactor associated with a metabolic reaction. The metabolite data 515 may include for each metabolite (for example) one or more of the following: the name of the metabolite, a description, neutral formula, charged formula, charge, spatial compartment of the biological system and/or module of the model, and identifier such as PubChem ID. Further, metabolite data 515 can identify an initial state value (e.g., an initial concentration and/or number of discrete instances) for each metabolite.

Reaction data 520 can identify each reaction (e.g., each metabolic reaction) associated with the model. For example, a reaction can indicate that one or more first metabolites is transformed into one or more second metabolites. The reaction need not identify one-to-one relationships. For example, multiple metabolites may be defined as reaction inputs and/or multiple metabolites may be defined as reaction outputs. The reaction data 520 may include for each reaction (for example) one or more of the following: the name of the reaction, a reaction description, the reaction formula, a gene-reaction association, genes, proteins, spatial compartment of the biological system and/or module of the model, and reaction direction. Further, the reaction data 520 can identify, for each metabolite of the reaction, a quantity of the metabolite, which may reflect the relative input-output quantities of the involved metabolites. For example, a reaction may indicate that two first metabolites and one second metabolite are input into a reaction and that two third metabolites are outputs of the reaction. The reaction data 520 can further identify an enzyme and/or cofactor that is required for the reaction to occur.

Functional gene data 525 can identify genes and relationships between genes, proteins, and reactions, which combined provide a biochemically, genetically, and genomically structured knowledge base or matrix. Functional gene data 525 may include (for example) one or more of the following: chromosome sequence data, the location, length, direction and essentiality of each gene, genomic sequence data, the organization and promoter of transcription units, expression and degradation rate of each RNA transcript, the specific folding and maturation pathway of RNA and protein species, the subunit composition of each macromolecular complex, and the binding sites and footprint of DNA-binding proteins. Network constructor 505 can use functional gene data and the availability of proteins encoded by those genes to update reaction constraints. One exemplary technique by which genomic data can be associated with reaction data is evaluating Gene-Protein-Reaction expressions (GPR), which associate reactions with specific genes that triggered the formation of one or more specific proteins. Typically a GPR takes the form (Gene A AND Gene B) to indicate that the products of genes A and B are protein sub-units that assemble to form a complete protein and therefore the absence of either would result in deletion of the reaction. On the other hand, if the GPR is (Gene A OR Gene B) it implies that the products of genes A and B are isozymes (i.e., each of two or more enzymes with identical function but different structure) and therefore absence of one may not result in deletion of the reaction. Therefore, it is possible to evaluate the effect of single or multiple gene deletions by evaluation of the GPR as a Boolean expression. If the GPR evaluates to false, the reaction is constrained to zero in the model.

A stoichiometry matrix controller 530 can use reaction data 520 to generate a stoichiometry matrix 535. Along a first dimension of the matrix, different compounds (e.g., different metabolites) are represented. Along a second dimension of the matrix, different reactions are represented. Thus, a given cell within the matrix relates to a particular compound and a particular reaction. A value of that cell is set to 0 if the compound is not involved in the reaction, a positive value if the compound is one produced by the reaction and a negative value if the compound is one consumed by the reaction. The value itself corresponds to a coefficient of the reaction indicating a quantity of the compound that is produced or consumed relative to other compound consumption or production involved in the reaction.

Because frequently relatively few reactions correspond to a given compound, stoichiometry matrix 535 can be a sparse stoichiometry matrix. Stoichiometry matrix 505 can be part of a set of model parameters (stored in a model-parameter data store 540) used to execute a module.

One or more modules may be configured to use linear programming 545 to identify a set of compound quantities that correspond to balancing fluxes identified in reactions represented in stoichiometry matrix 535. Specifically, an equation can be defined whereby the product of stoichiometry matrix 535 and a vector representing a quantity for each of some of the compound quantities is set to zero. (It will be appreciated that the reactions may further include quantities for one or more boundary metabolites, for which production and consumption need not be balanced.) There are frequently multiple solutions to this problem. Therefore, an objective function is defined, and a particular solution that corresponds to a maximum or minimum objective function is selected as the solution. The objective function can be defined as the product between a transposed vector of objective weights and a vector representing the quantity for each compound. Notably, the transposed vector may have a length that is equal to the first dimension of stoichiometry matrix 535, given that multiple reactions may relate to a same compound.

The objective weights may be determined based on objective specifications 550, which may (for example) identify one or more reaction-produced compounds that are to be maximized. For example, the objective weights can be of particular proportions of compounds that correspond to biomass, such that producing compounds having those proportions corresponds to supporting growth of the biological system.

Each reaction may (but need not) be associated with one or more of a set of reaction constraints 555. A reaction constraint may (for example) constrain a flux through the reaction and/or enforce limits on the quantity of one or more compounds consumed by the reaction and/or one or more compounds produced by the reaction.

In some instances, linear programming 545 uses stoichiometry matrix 535 and reaction constraints 550 to identify multiple solutions, each complying with the constraints. When multiple solutions are identified, objective specifications 550 can be used to select from amongst the potential solutions. However, in some instances, no solution is identified that complies with stoichiometry matrix 535 and reaction constraints 555 and/or the only solution that complies with the matrix and constraints is not to proceed with any reaction.

A solution can include one in which, for each of a set of metabolites, a consumption of the metabolite is equal to a production of the metabolite. That is not to say that this balance must be achieved for each metabolite, as a set of reactions involve one or more "boundary metabolites" for which this balance is not achieved. For example, glucose can be consumed at a given rate, and/or acetate can be produced at a given rate.

Reaction data 520 may further identify an objective function that identifies a target product (e.g., representing cell growth rate) that is to be maximized. The objective function can identify particular ratios of multiple reactant metabolites that must be available to produce the product. Strictly enforcing the objective function may result in simulating no growth if a single metabolite is not produced. An alternative approach is to define one or more objective functions configured such that production of each of multiple target reactant metabolites that relate to the target product is to be maximized. A higher level whole-cell model can evaluate the production of multiple target reactant metabolites to determine whether to and/or an extent to which to simulate growth. For example, depending on which target reactant metabolite(s) are not produced, the whole-cell model may nonetheless simulate cell growth, simulate cell growth at a reduced rate, simulate no growth, simulate unhealthy or impaired growth or simulate cell death.

For example, a reaction space can be defined based on stoichiometry matrix 535 and reaction constraints 555. The space may have as many dimensions as there are reactions. Each dimension can be restricted to include only integer values that extend along a range constrained by any applicable constraint in reaction constraints 555. A reaction space sampler 560 can then determine, for each of some or all of the points within the reaction space, a cumulative quantity of each metabolite that would be produced based on the associated reactions. Reaction space sampler 560 can compare these quantities to those in the objective vector (e.g., by determining an extent to which proportions of compounds are consistent).

In these instances, a scoring function 565 can indicate how to score each comparison. For example if proportions of each of two potential solutions differ from the objective proportions by 2, but one potential solution differs by 2 for a single compound and another by 1 for each of two compounds, scoring function 565 can be configured to differentially score these instances. For example, different weights may be applied to different compounds, such that differences that affect a first compound are more heavily penalized than differences that affect a second compound. As another example, scoring function 565 may indicate whether a score is to be calculated by (for example) summing all compound-specific (e.g., weighted) differences, summing an absolute value of all compound-specific (e.g., weighted) differences, summing a square of all compound-specific (e.g., weighted) differences, etc. Reaction space sampler 560 can then identify a solution as corresponding to reaction coefficients that are associated with a highest score across the reaction space.

Network constructor 505 can receive results from each of linear programming 545 and/or reaction space sample 560. In some instances, linear programming 545 can further avail its results to reaction space sample 560. When a balanced solution is identified by linear programming 545, reaction space sampler 560 need not sample the reaction space and need not avail reaction-space results to network constructor 505.

Network constructor 505 can identify a solution as corresponding to one identified by linear programming 545 when a balanced solution is identified and as a highest-score potential solution identified by reaction space sampler 560 otherwise. The solution can then indicate the compounds produced by and consumed by the reactions performed in accordance with the solution-indicated flux. Network constructor 505 can update metabolite data 515 based on this production and consumption.

In some instances, a solution is identified for each of a set of time points rather than only identifying one final solution. The iterative time-based approach may be useful when module-specific simulation controller 500 is but one of a set of simulation controllers and metabolite data 515 is influenced by the performance of other modules. For example, metabolite data 515 may be shared across modules or may be defined to be a copy of at least part of a cross-module metabolite data set at each time point. The updates to the metabolites performed by network constructor 505 may then be one of multiple updates. For example, an update by network constructor 505 may indicate that a quantity of a specific metabolite is to increase by four, while a result from another module indicates that a quantity of the specific metabolite is to decrease by two. Then the metabolite may change by a net of +2 for the next time iteration.

A results interpreter 570 can generate one or more results based on the updated metabolite data 515. For example, a result may characterize a degree of growth between an initial state and a steady state or final time point. The degree of growth may be determined based on a ratio between values of one or more metabolites at a current or final time point relative to corresponding values at an initial (or previous) time point. The one or more metabolites may correspond to (for example) those identified in an objective function as corresponding to biomass growth. As another example, a result may characterize a time course of growth. For example, a result may identify a time required for metabolite changes that correspond to a representation of a double in growth or a time constant determined based on a fit to values of one or more time series of metabolite values. The result(s) may be output (e.g., locally presented or transmitted to a remote device, such as a user device). The output can facilitate a presentation of an interface that indicates one or more simulation characteristics (e.g., one or more default values in terms of initial-state values or reaction data and/or one or more effected perturbations).

Operation of module-specific simulation controller 500 can be influenced by particular simulated perturbations of the whole cell. For example, each perturbation may correspond to a particular type of genetic mutation. The perturbation may have been identified based on detecting user input (e.g., a selection and/or text input received via an interface) that defines the perturbation. One exemplary type of perturbation is a gene mutation. An effect of the perturbation may be determined based on functional gene data (e.g., to determine how an availability of one or more metabolites is affected). High-level metabolite data, simulator parameters and/or high-level constraints may then be accordingly set, constrained and/or defined based on the perturbation. This high-level perturbation can thus then influence operation of one or more lower level modules.

Figure 6:
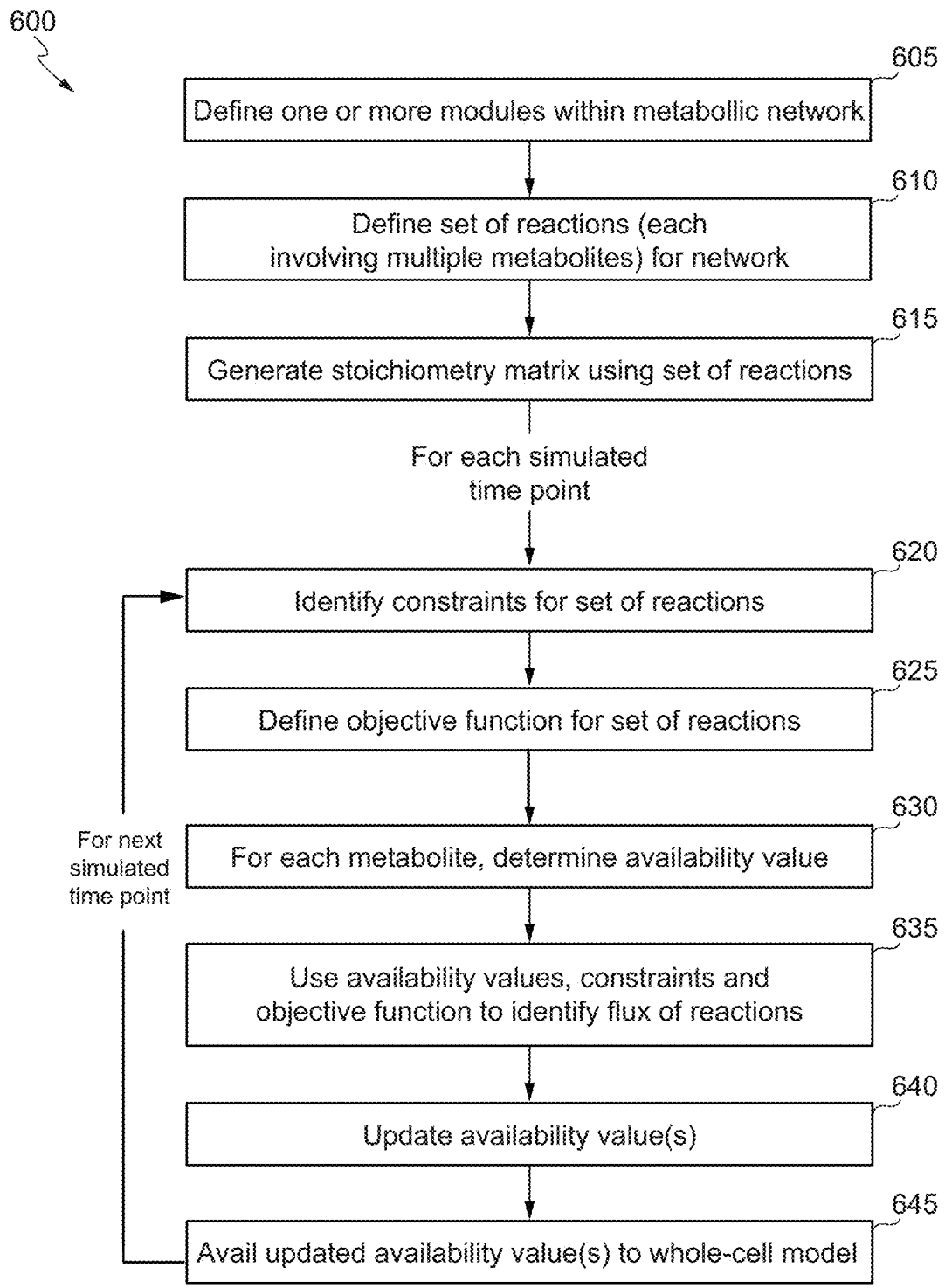
FIG. 6 shows a process for using a simulator to generate metabolite time-course data according to various embodiments.

FIG. 6 shows a process 600 for using a simulator to generate metabolite time-course data according to various embodiments. In some embodiments, the processes depicted in process 600 are implemented by the interaction system 100 of FIG. 1, and discussed with respect to the module-specific simulation controller 500 of FIG. 5. Process 600 begins at block 605, at which a one or more modules within a metabolic network (e.g., of a biological system) are defined. The module(s) can be defined based on which parts of the network exhibit relative functional independence and/or correspond to substantial independence in terms of biological activity. In some instances, a default is to define each part of a cell as part of a core module unless a different module corresponding to particular types of actions and/or cell components is defined.

At block 610, a set of reactions is defined for the network. In some instances, the set of reactions are defined for the module (or each module) that corresponds to the default model type. The set of reactions can indicate how various molecules such as metabolites are consumed and produced through part of all of a life cycle of a biological system. Each reaction thus identifies one or more metabolites that are consumed, one or more metabolites that are produced and, for each consumed and produced metabolite, a coefficient (which may be set to equal one) indicating a relative amount that is consumed or produced. The reaction may further include an identification of one or more enzymes, one or my cofactors and/or one or more environmental characteristics that are required for the reaction to occur and/or that otherwise affects a probability of the reaction occurring or a property of the reaction. The reactions may be identified based on (for example) online or local digital content (e.g., from one or more scientific papers or databases) and/or results from one or more wet-lab experiments.

At block 615, a stoichiometry matrix is generated using the set of reactions. Each matrix cell within the matrix can correspond to a particular metabolite and a particular reaction. The value of the cell may reflect a coefficient of the particular metabolite within the particular reaction (as indicated in the reaction) and may be set to zero if it is not involved in the reaction. In some instances, metadata is further generated that indicates, for each of one or more reactions, any enzyme, co-factor and/or environmental condition required for the reaction to occur.

At block 620, one or more constraints are identified for the set of reactions. In some instances, identifying the constraints may include identifying values for one or more parameters. For example, for each of one or more or all of the set of reactions, a constraint may include a flux lower bound and/or a flux upper bound to limit a flux, a quantity of a consumed or produced metabolite, a kinetic constant, a rate of production or decay of a component such as RNA transcript, an enzyme concentration or activity, a compartment size, and/or a concentration of an external metabolite. The constraint(s) may be identified based on (for example) user input, online or local data, one or more communications from a wet-lab system, and/or learned from statistical inference.

At block 625, an objective function is defined for the set of reactions. The objective function may identify what is to be maximized and/or what is to be minimized while identifying a solution. The objective function may (for example) identify a metabolite that is produced by one or more reactions or a combination of metabolites that is produced by one or more reactions. The combination may identify proportions of the metabolites. However, the objective function can have a number of limitations and may fail to reflect supply and demand within the other modules. Thus, in some instances, a limited objective function can be constructed to include a set of target values for each molecule within the metabolic network. The target values can incorporate intrinsic-rate parameters, supply rates of molecules, the consumption rates of molecules, and the molecule concentrations into a measurement of target concentrations of the molecule given supply, demand, and an "on-hand" concentration of each molecule, which represents the concentration of a molecule immediately available to a reaction pathway. The target values may be calculated and incorporated into the objective function to produce the limited objective function. This may be in the form of calculating an absolute difference between the target value and the proportional flux contribution of each molecule. This may be in the form of scaling the proportional flux contribution of each molecule. This may be in the form of adding to the proportional flux contribution of each molecule. Any other mathematical modification of the proportional flux contribution of each molecule that adjusts this value by the target value may be used. The target values may be positive or negative. For purposes of unit conversion, so that target values can be included in the objective function and compared to the flux values, the target values may be constructed as rates.

At block 530, for each metabolite related to the set of reactions, an availability value is determined. For an initial value, the value may be identified based on (for example) user input, digital content and/or communication from another system. Subsequent values may be retrieved from a local or remote data object that maintains centralized availability values for the set of metabolites.

At block 635, the availability values, constraints and objective function are used to determine the flux of one, more or all of the set of reactions. The flux(es) may indicate a number of times that each of one, more or all of the reactions were performed in a simulation in accordance with the availability values, constraints and objective function. The flux(es) may be determined based on a flux-balance-analysis model. In some instances, the flux(es) may be determined based on a sampling of all or part of an input space representing different flux combinations and scoring each input-space using a scoring function.

At block 640, a centralized availability value of one or more metabolites is updated based on the determined flux(es). More specifically, for each metabolite, a cumulative change in the metabolite's availability may be identified based on the cumulative consumption and cumulative production of the metabolite across the flux-adjusted set of reactions. The centralized availability value of the metabolite can then be incremented and/or decremented accordingly.

In some instances, at least one the one or more modules defined at block 605 are to be associated with a model that does not depend on (for example) a stoichiometry matrix and/or flux based analysis and/or that is based on physiological modeling. One or more modules based on one or more different types of models can also, at each time point, identify a change in metabolite availability values, and such changes can also be used to update a local or remote data object with centralized availability values. With respect to each metabolite, updates in availability values may be summed to identify a total change and/or updated availability value. In some instances, limits are set with respect to a maximum change that may be effected across subsequent time steps and/or a maximum or minimum availability value for a metabolite.

At block 645, availability data is availed to a higher-level model. State vectors can then be updated based on data from multiple modules.

Some or all of blocks 620-645 may be repeated for each of multiple simulated time points in a simulation. Thus, at each time point, constraints can be updated based on state-vector information (e.g., representing availability of catalysts), an objective function can be defined (e.g., which may change across time points based on a configuration of a higher level objective), updated metabolite availability values can be determined, updated reaction fluxes can be identified, and further updated availability values can be determined. In some instances, a predefined number of simulated time points are to be evaluated and/or simulated time points corresponding to a predefined cumulative time-elapsing period are to be evaluated. In some instances, a subsequent simulated time point is to be evaluated until a predefined condition is satisfied. For example, a predefined condition may indicate that metabolite values for a current simulated time point are the same or substantially similar as compared to a preceding simulated time point or a preceding simulated time period.

With regard to a repeated iteration of block 630, it will be appreciated that an availability value determined for a given metabolite need not be equal to the corresponding updated availability value from the previous iteration of block 640 and/or the sum of the previously determined availability value adjusted by the identified flux pertaining to the metabolite. Rather, a processing of the previous time point with respect one or more other modules may have also resulted in a change in the metabolite availability, and/or a higher level constraint and/or processing may influence the availability. Thus, the availability value for a given metabolite determined at block 630 for a current time point may be equal to the availability value determined at block 630 for a preceding time point plus the cumulative updates to the availability value across modules, with any limits imposed.

While not shown in process 600, one or more variables can be output (e.g., transmitted to a user device). The variable(s) may include final values (e.g., availability values after all iterations have been performed), time-course values, high-level values and/or module-specific values. For example, the availability data may include, for each of one, more or all metabolites: an availability value (e.g., a final availability value) and/or a time course of the availability value. In some instances, the availability data is output with reference availability data. For example, when part or all of the processing performed to calculate the availability values was associated with a perturbation, the reference availability data may be associated with an unperturbed state. In some instances, a processed version of the availability data is output. For example, a comparison of availability values for particular metabolites across time points may be used to generate one or more growth metrics (e.g., a growth magnitude or rate), which may be output. Outputting the availability data can include (for example) locally presenting the availability data and/or transmitting the availability data to another device.

III. Continuous Culture System

Figure 7:
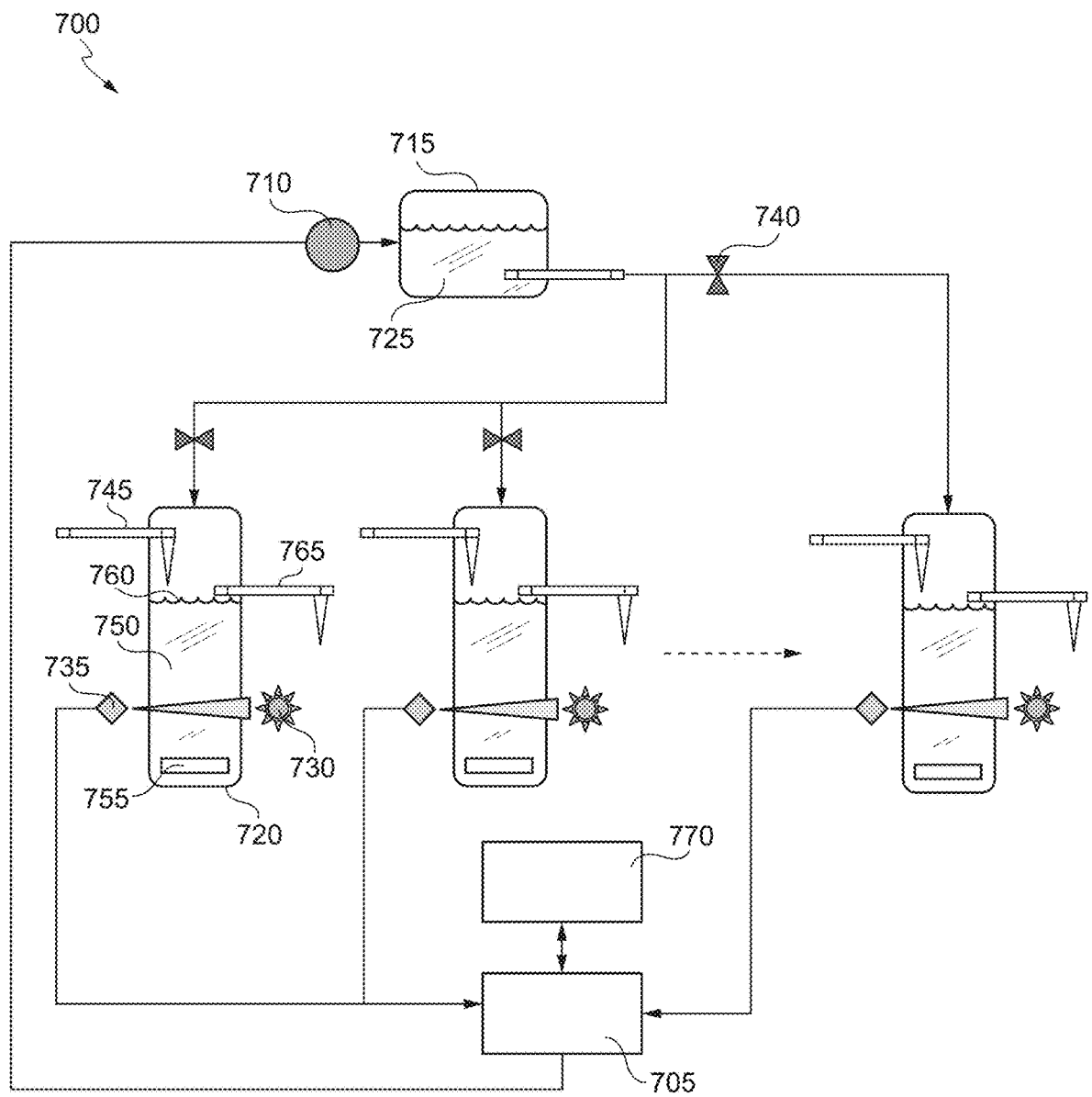
FIG. 7 shows a culture system according to various embodiments.

A primary tool for culturing a biological system (e.g., cells) in a static environment is a culture system such as a continuous culture system, where inoculated growth medium is continually diluted with fresh medium. At steady state, a continuous culture system will dilute cells and waste products at the same rate that they are being produced leading to an unchanging environment or a physiological steady state where growth of the biological system is occurring at a substantially constant growth rate. FIG. 7 shows a culture system 700 in accordance with aspects of the present disclosure. In various embodiments, the culture system 700 is a continuous culture system. In some embodiments, the culture system 700 is a turbidostat. A turbidostat uses a feedback control loop to keep cell density constant within the culture. Cell density determines the turbidity of the culture. In order to maintain a constant cell density, the turbidity of the culture is monitored and used to compute a dilution rate that achieves or maintains a predetermined cell density. Thus, a turbidostat is an ideal culture system for characterization of biological systems without nutrient limitation, when cells are growing at their maximum rate.

In some embodiments, the culture system 700 includes an electronics module 705, one or more pumps 710, a fresh medium reservoir 715, and one or more culture chambers 720 (although only three culture chambers 720 are shown, it should be understood that there could be any number of culture chambers 720). The electronics module 705 may include software and/or electronic circuit components such as discrete and/or integrated electronic circuit components that implement analog and/or digital circuits capable of producing the functions attributed to the culture system 700 such as measuring optical density (OD), computing dilution rates, and controlling the flow of fresh medium 725 from the reservoir 715 to the culture chambers 720. In some embodiments, the software and/or electronic circuit components include: (i) an OD measurement tool that measures the OD of each culture chamber 720 using a light source 730 and an optical sensor 735, (ii) a user programmable module that determines dilution rates based on the optical densities, (iii) embedded circuitry used to control the one or more pumps 710 and/or valves 740 based on the determined dilution rates for each culture chamber 720, and (iv) a non-transitory memory with program instructions operable on by the controller to perform one or more processes for controlling the culture system 700.

The operation of the culture system 700 may be based upon a dilution cycle with an adjustable period and a desired OD or turbidity. The adjustable period may be determined based on a preselected time parameter (e.g., every 1, 2, 3, or 4 hours) or based on a function of cell growth (e.g., after every 10 cell doublings). In some embodiments, the period is at least 10 cell doublings. The period may also be determined based upon the type of medium being used to grow the culture. The desired OD may be determined based on a preselected turbidity parameter or specific growth rate. In some embodiments, the operation of the culture system 700 includes measuring, for a dilution cycle or multiple dilution cycles, an actual OD of each of the culture chambers 720. For example, at the start of each period, the actual OD of each of the culture chambers 720 may be measured using the light source 730 and the optical sensor 735. The specific growth rate of each of the culture chambers 720 is at or substantially close to μmax (maximum specific growth rate), which is controlled by the rates of internal cellular reactions as they are expressed in the OD of the culture biomass (that is, the turbidity of the culture). In some embodiments, the operation of the culture system 700 further includes determining, for each culture chamber 720, a dilution rate as a function between the desired OD and the actual OD. For example, for each culture chamber 720, when actual measured OD reaches a certain level beyond the desired OD (predetermined OD), the electronics module 705 determines a dilution rate as a function between desired OD (predetermined OD) and actual measured OD.

The dilution rates, which may be different for each culture chamber 720, are then sent to the embedded circuitry. In some embodiments, the operation of the culture system 700 further includes controlling a pump 710, a valve 740, or a combination thereof to provide fresh medium 725 to the culture chambers 720 at the dilution rate for each of the culture chambers 720 to return a turbidity of the biological system in each of the culture chambers 720 to the desired OD. For example the embedded circuitry may control the pumps 710 and/or valves 740 to provide fresh medium 725 from the reservoir 715 to each of the culture chambers 720 at the respective determined dilution rates in order to return the turbidity to the required level (the desired OD). The aim is to hold culture turbidity constant by manipulating the rate at which medium is fed. If the turbidity tends to increase, the feed rate of fresh medium 725 is increased to dilute the turbidity back to its set point. When the turbidity tends to fall, the feed rate of fresh medium 725 is lowered so that growth can restore the turbidity to its set point. As new medium 725 is added to each of the culture chambers 720 via input 745, the medium may be mixed by a stirrer 745 diluting old medium, cells, and waste products 750. When the medium level 755 rises to the output 760, the fresh medium 725 mixed with the old medium, cells, and waste products 750 is forced out of the culture chamber 720. These turbidity measurements are taken at the beginning of each period and dilution rates are adjusted accordingly to maintain each of the culture chambers 720 at steady state.

In various embodiments, the culture system 700 further includes an analyzer 765. In some embodiments, the operation of the culture system 700 further includes measuring, by the analyzer 765, one or more characteristics in a sample of the cells from one or more of the culture chambers 720 to obtain at least some measurement data. The analyzer 765 may include one or more measuring modules for taking measurements of the cells from the culture chambers 720. For example, the measuring modules may include a flow cytometer, an immunoassay, an optical assay such as a fluorescence assay, a sequencer, a microscope, quantitative western blots, protein assays, or the like, and combinations thereof. The measuring modules may be integrated with the culture chambers 720 such that the measurements can be taken directly from cells within the chambers during culture cycling and/or the measuring modules may be separate from the culture chambers 720 such that the measurements can be taken from samples (i.e., harvested cells) obtained from the culture chambers 720. The measurements may be taken after a predetermined number of dilution cycles. For example, the measurement may be taken after 1, 5, 10, 15, or 20 dilution cycles. In certain embodiments, the measurements are taken after at least one dilution cycle. The predetermined amount of time may be determined based on amount of fresh medium 725 available for diluting the cell cultures and/or a mutation rate for the cells.

The measurements to be taken of the cells may be determined based on a model of a biological system. As described herein, a biological system such as a living cell, or a population of living cells, can be modeled in silico such that the response of the living cell(s) to a variety of experiments can be performed quickly and cheaply in simulation. The structure of the model in terms of the mathematical representation of the function, which describes the system components and relationships, may be defined according to current knowledge, conceivably in combination with data-driven network inference techniques that aim to learn the likely structure of a system from observations of its variables. However, a user attempting to model a biological system also needs to obtain suitable estimates for the parameters (e.g., kinetic parameters), either from experimentally determined values or by using statistical approaches to estimate (or infer) these values by fitting model simulations to observed data.

In various embodiments, techniques are provided for making use of in vivo data from the target cells of interest (cultured in the culture system 700) where available to experimentally estimate parameters in the correct cellular context. For example, a model of a biological system may be analyzed (e.g., analyzed by a controller such as simulation controller 105 described with respect to FIG. 1) to identify a parameter having an unknown value. The model predicts a response of the biological system to a set of conditions based on a plurality of parameters including the identified parameter, and the identified parameter models an aspect of structure or function of the biological system. Once the parameter having an unknown value is identified, one or more characteristics of the biological system that are related to the identified parameter and measurable in the culture system may be determined. As should be understood, not all parameters are directly measurable in an experimental system, and thus one or more characteristics can be determined from which the identified parameter may be estimated. Thereafter, measurement data is obtained (e.g., RNA sequencing data) that is indicative of the one or more characteristics of the biological system developed in the culture system 700. The measurement data can be obtained by the one or more measuring modules of the analyzer 765. The measurement data is indicative of the one or more characteristics at a physiological steady state where growth of the biological system is occurring at a substantially constant growth rate since the measurements are obtained from the cell culture 700. A value for the identified parameter can be determined (i.e., estimated) based on an growth formula, the measurement data, and the substantially constant growth rate. Once the value is determined for the identified parameter, the model can be built with parametrization constraint based on the estimated value for the identified parameter, as described in further detail below with respect to FIG. 8

While the culture system 700 is described at some length and with some particularity with respect to a turbidostat, it is not intended that the culture system 700 be limited to a turbidostat or any such particular culture components or configuration. Instead, it should be understood that the described embodiments are provided as examples of a culture system; the components and configuration described with respect to the culture system are to be construed with the broadest sense to include variations of the particular components and configuration. For example, a chemostat may be used to maintain a steady state or a different control system (e.g., measuring pH or carbon dioxide) may be used to monitor biomass and control medium supply to maintain a steady state.

IV. Parameter Estimation

Figure 8:
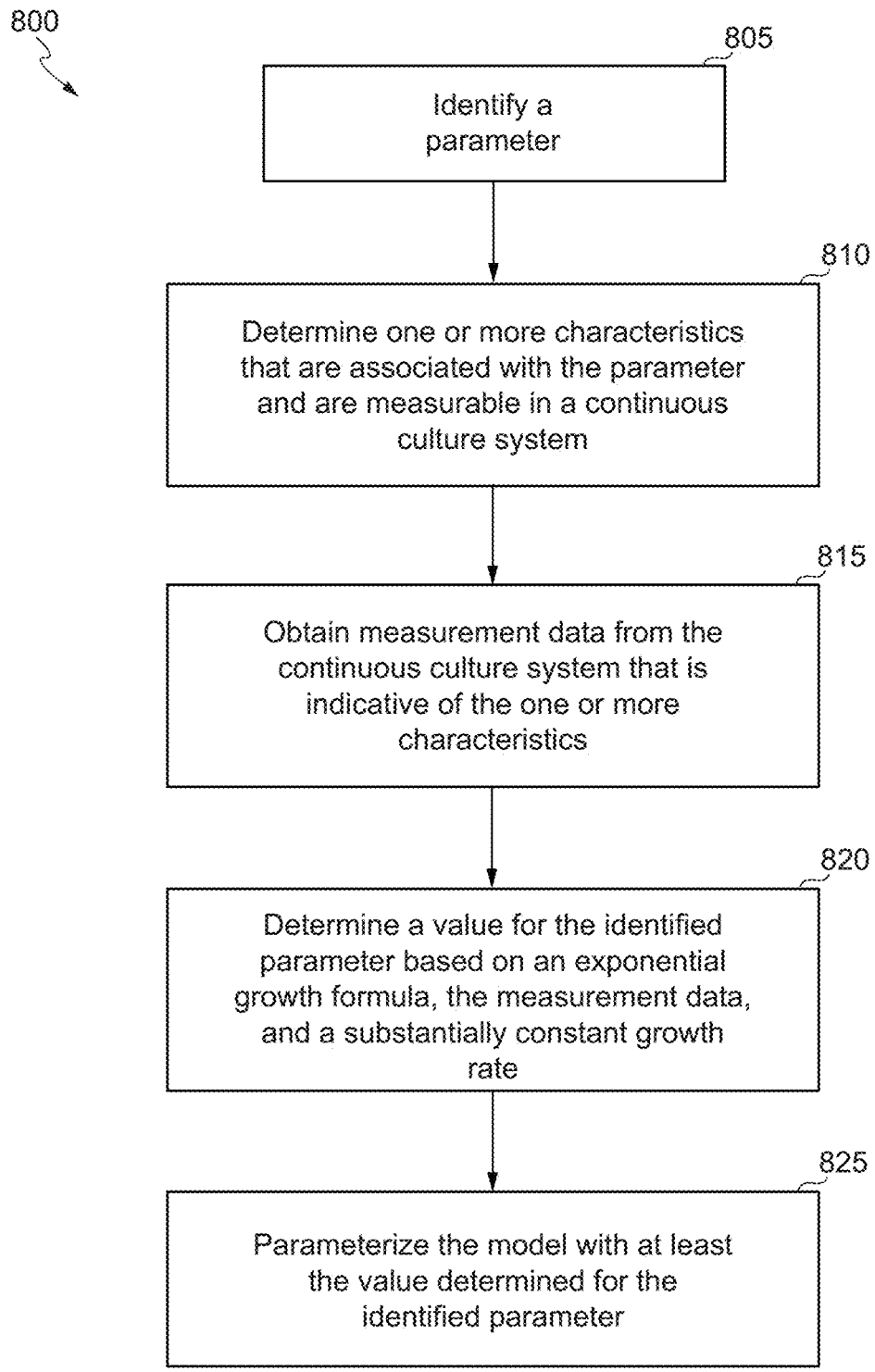
FIG. 8 shows a process using measurements taken from a culture system to estimate parameters for a model according to various embodiments.

FIG. 8 is a simplified flow chart 800 illustrating an example of processing for using measurements taken from a culture system (e.g., the culture system 700 described with respect to FIG. 7) to estimate parameters for a model (e.g., estimate parameters used by simulation controller 105 and/or simulation controller 300 to model a biological system as described with respect to FIGS. 1-6) according to various embodiments. Process 800 begins at block 805, at which a parameter is identified. The identifying of the parameter may include analyzing a model of a biological system to identify a parameter. In some embodiments, the parameter has an unknown value (e.g., a value has not yet been provided for the parameter). In some embodiments, the computing system automatically analyzes the model and identifies a parameter. In other embodiments, the computing system is assisted by a user (e.g., via a user interface) in analyzing the model and identifying the parameter. As should be understood, more than one parameter may be identified, and thus, the following steps may be performed iteratively to estimate a value for each of the parameters having an unknown value.

The model predicts a response of the biological system to a set of conditions based on a plurality of parameters including the identified parameter, and the identified parameter models an aspect of structure or function of the biological system. In some embodiments, the identified parameter is tied to one or more modules (e.g., a transcription module) being used to model one or more biological processes (e.g., production of a protein) of the biological system. Thus, analysis of the model may include identifying parameters that are necessary for producing a model capable of simulating the one or more biological processes. Exemplary specific parameters may include an amount and/or number of discrete instances of a constituent (e.g., a protein, a particular sequence of RNA, a metabolite, an ion, etc.) in the biological system, intrinsic rates, kinetic constants, concentrations of external metabolites, compartment sizes, a reaction rate of an enzyme, an affinity of an enzyme for a substrate or cofactor, a relationship between a DNA or RNA sequence and the function or properties of a related protein, a pH-dependence of the function of an enzyme or membrane protein, or some other properties of elements of the biological system.

At block 810, one or more characteristics of the biological system are determined that are associated with the identified parameter and are measurable in a culture system. The one or more characteristics are indicative of the cell state or physiology and are determined to be associated with the identified parameter in such a manner that the one or more characteristics can be used to estimate a value for the identified parameter. Exemplary specific characteristics may include a growth rate of a cell, RNA sequencing (RNA SEQ, also called whole transcriptome shotgun sequencing (WTSS), uses next-generation sequencing (NGS) to reveal the presence and relative amount of each transcript in a biological sample at a given moment), metabolite or molecule concentrations, proteomics, and cell composition such as total cellular protein, total cellular RNA, total cellular DNA, and dry cell weight. In some embodiments, the computing system automatically determines the one or more characteristics associated with the identified parameter. In other embodiments, the computing system is assisted by a user (e.g., via a user interface) in determining the one or more characteristics associated with the identified parameter.

In some embodiments, the one or more characteristics of the biological system may be determined based on a knowledge corpus for the model that identifies components of reactions or processes in the biological system. The knowledge corpus may include reactions or processes, the reactants, and the products that are associated with a parameter such as a reaction or kinetic rate. For example, if the parameter having an unknown value is identified as a synthesis rate of a particular transcript $T_1$, then the one or more characteristics determined from the knowledge corpus to be associated with the synthesis rate of transcript $T_1$ may include growth rate of the cell, total cellular RNA, and RNA SEQ data for $T_1$. The growth rate and the total cellular RNA can be used to estimate a rate of RNA synthesis, and the rate of RNA synthesis and the RNA SEQ data can be used to estimate the rate of production of the transcript $T_1$, as described in further detail with respect to FIG. 9.

At block 815, measurement data is obtained for the one or more characteristics of a biological system developed in the culture system. In some embodiments, the biological system being modeled in silico and the biological system being developed in the culture system are the same biological system (e.g., a same cell type or same cell type population) or substantially the same biological system (e.g., a first cell type and a minor variant of the first cell type). The measurement data may be obtained from a culture system once the biological system has achieved a physiological steady state. Furthermore, the measurement data may be obtained from a same sample (e.g., growth rate, total cellular RNA, and total cellular DNA are obtained from a same sample) to assure that the one or more characteristics are reflective of what the cells are doing at the time of measurement. Thus, the measurement data is indicative of the one or more characteristics at a physiological steady state where growth of the biological system is occurring at a substantially constant growth rate.

For example, measurements can be taken directly from cells within the culture chambers during culture cycling and/or taken from samples of cells (i.e., harvested cells) obtained from the culture chambers. The measurements may be taken after a predetermined number of dilution cycles once the biological system has achieved a physiological steady state. For example, the measurement may be taken after 1, 5, 10, 15, or 20 dilution cycles. The predetermined number of dilution cycles may be also be dependent upon an amount of fresh medium available for diluting the cell cultures and/or a mutation rate for the cells. Additionally or alternatively, the measurement data may be obtained from a data structure that stores historical measurement data taken after a predetermined number of dilution cycles once the biological system of one or more culture systems has achieved a physiological steady state. Additionally or alternatively, the measurement data may be obtained from a data structure (e.g., the knowledge corpus) that stores known measurement data (e.g., a known nucleic acid sequence for DNA or DNA, a known amino acid sequence for a protein, or a known mass for an amino acid or similar molecule).

At block 820, a value for the identified parameter is determined or estimated based on an growth formula, the measurement data, and the substantially constant growth rate. Since the measurement data is obtained at a physiological steady state, it is understood that every component of the biological system is growing at a same growth rate and this can be used to estimate many unknown parameters. More specifically, an growth formula or equation can be generated for many (if not all) intrinsic properties (e.g., the identified parameter) of the biological system in the cell culture. The growth formula or equation can be generated to scale at the same rate as the substantially constant growth rate, and allows for the time component of parameter estimation to be removed from the measurements. In some embodiments, the growth formula or equation is an exponential growth formula or equation that is generated to scale at the same exponential rate as the substantially constant growth rate. Moreover, the use of measurement data taken at physiological steady state allows for the value of the parameter to be estimated without having to be concerned with relaxation times (which are prominent in single stage or batch experiments).

At block 825, the model is parametrized with at least the value determined for the identified parameter. For example, a module-specific simulator controller (as described with respect to FIG. 3) can identify, for each module, one or more simulation parameters and an input data set. The simulation parameters may include the identified parameter and the value determined for the identified parameters may be retrieved from a local data store (e.g., a simulator parameters data store) or from a remote source. The value for the parameter, once selected and input into the model, may be fixed across time-step iterations. Upon identifying an input data set and the parameters including the identified parameter, a module-specific simulator controller can run a simulation assigned to the module selected using the input data set and at least the value determined for the identified parameter for simulating at least a portion of the model.

Figure 9:
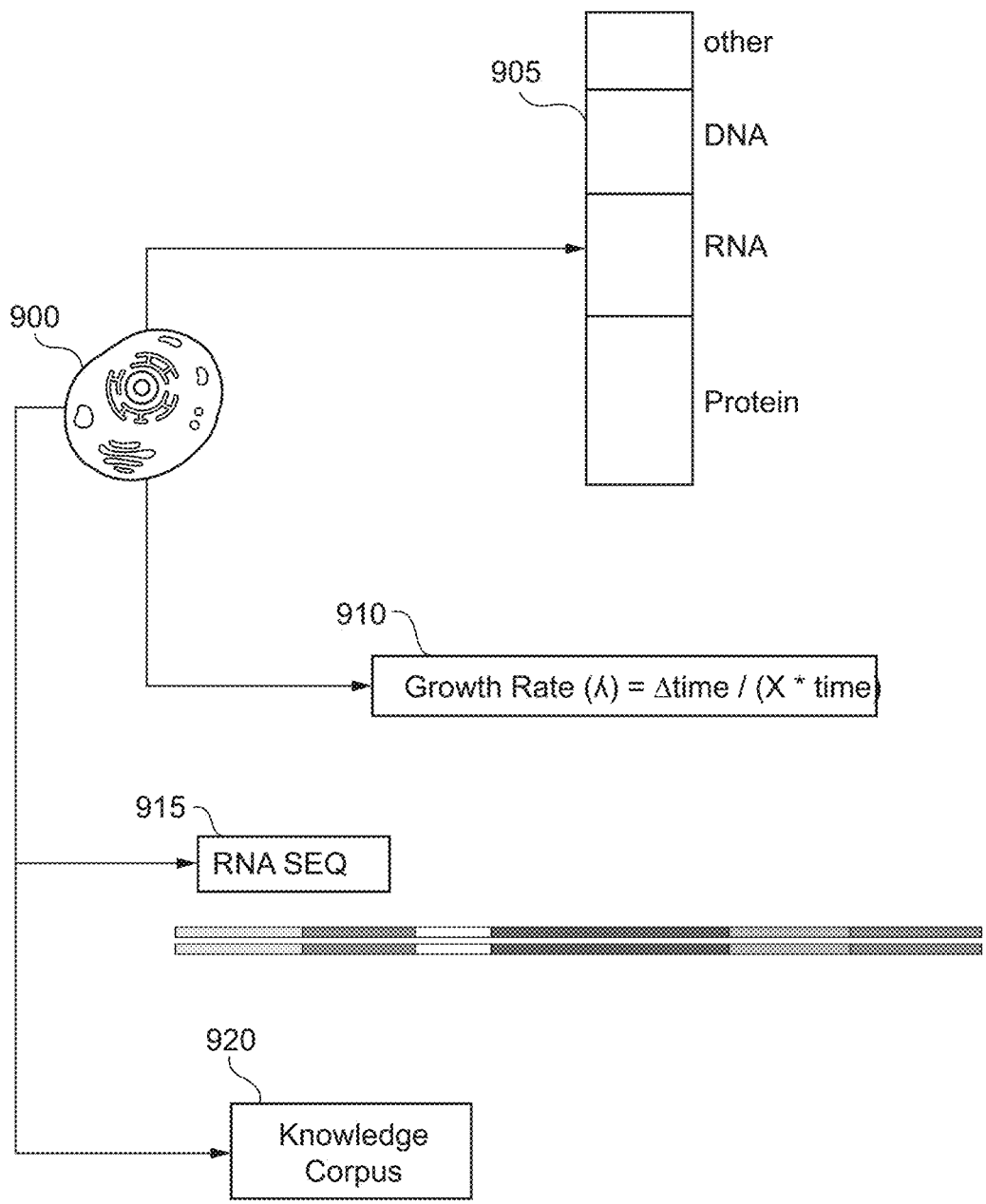
FIG. 9 demonstrates how a modeling system can use high-level measurements from a cell culture at a physiological steady state to determine (estimate) specific parameters for constraining a model according to various embodiments.

FIG. 9 demonstrates how a system (e.g., the modeling system described with respect to FIGS. 1-6) can use high-level measurements from a cell culture 900 (e.g., the culture system 700 described with respect to FIG. 7) at a physiological steady state to determine (estimate) specific parameters (e.g., rate constants) for constraining a model. The one or more characteristics may include cell composition 905 such as total cellular protein, total cellular RNA, total cellular DNA, and other measurable constituents, (e.g., dry cell weight). For example, one or more measuring modules for taking measurements of cells from the culture chambers may generate measurement data that includes on average each cell has 10 fg ($10^{-15}$) of RNA/cell. Additionally, the one or more characteristics may include a growth rate 910 of the biological system 900. For example, one or more measuring modules for taking measurements of cells from the culture chambers may calculate measurement data that includes on average each cell has a substantially constant growth rate ($\hat{K}$). The growth rate ($\hat{K}$) can be expressed as:

$$\text{growth rate}(\hat{K}) = \Delta\text{time}/(X^*\text{time}) \quad \text{(Equation 1)}$$

where $\Delta$time is change in time, over an amount of substance X multiplied by a unit time. Since the measurement data is obtained at a physiological steady state, it is understood that every component of the biological system or cell is growing at a same growth rate and this can be used to estimate many unknown parameters including rate constants such as average rate of RNA synthesis per unit time. For example, the system can determine that an average rate of RNA synthesis per unit time can be expressed as the following exponential growth formula:

$$10 \text{ fg}(10^{-15}) \text{ of RNA/cell}^*\text{Growth Rate}(\hat{K}) \text{ or}$$
$$\{0.1 \text{ fg}(10^{-15})\text{RNA}/(1 \text{ fg}(10^{-15})\text{RNA}^*s)\} =$$
$$1 \text{ fg}(10^{-15})\text{RNA}/s \quad \text{(Equation 2)}$$

where 10 fg ($10^{-15}$) of RNA/cell is the average measured amount of RNA in the cell, 0.1 fg ($10^{-15}$) RNA/(1 fg ($10^{-15}$) RNA*s) is the average calculated growth rate of the cell, and 1 fg ($10^{-15}$) RNA/s is the average amount of RNA synthesized (added to the cell) every second.

Additionally, the one or more characteristics may include RNA SEQ 915, which is a relative abundance of each of the transcripts in the cell. For example, one or more measuring modules for taking measurements of cells from the culture chambers may generate measurement data that includes on average each cell has a relative abundance of 0.001 for a particular transcript $T_1$. The system can determine that an average rate of transcript $T_1$ synthesis per unit time can be expressed as:

$$0.001 \text{ of transcript } T_1 * 1 \text{ fg}(10^{-15})\text{RNA}/s = 1 \text{ ag}(10^{-18})$$
$$\text{transcript } T_1/s \quad \text{(Equation 3)}$$

where 0.001 of transcript $T_1$ is the relative amount of transcript $T_1$, 1 fg ($10^{-15}$) RNA/s is the average amount of RNA synthesized (added to the cell) every second, and 1 ag ($10^{48}$) transcript $T_1/s$ is the average amount of transcript $T_1$ synthesized (added to the cell) every second. The average amount of transcript $T_1$ synthesized (added to the cell) every second is a rate constant and can subsequently be used as a value for an identified parameter in order to parameterize the model (constrain the model to a known term).

Moreover, the one or more characteristics may include information obtained directly from the knowledge corpus 920. For example, the system may obtain measurement data from the knowledge corpus 920 that includes a mass $M_{T1}$ for transcript $T_1$ or the amino acid sequence for transcript $T_1$ and mass for each amino acid such that the system can calculate the mass $M_{T1}$ for transcript $T_1$. The system can determine that an average count of transcript $T_1$ synthesis per unit time can be expressed as:

$$(1 \text{ ag}(10^{-18})\text{transcript } T_1/s)/M_{T1} = \text{count of transcript}$$
$$T_1/s \quad \text{(Equation 4)}$$

where 1 ag ($10^{-18}$) transcript $T_1/s$ is the average amount of transcript $T_1$ synthesized (added to the cell) every second, $M_{T1}$ is the mass of 1 molecule of transcript $T_1$, and the count of transcript $T_1/s$ is the average count of transcript $T_1$ synthesis per unit time. The average count of transcript $T_1$ synthesis per unit time is a steady state synthesis rate for transcript $T_1$ and can subsequently be used as a value for an identified parameter in order to parameterize the model (constrain the model to a known term).

While the techniques for estimating parameters are described at some length and with some particularity with respect to RNA transcripts, it is not intended that the techniques be limited to RNA transcripts or any such particular rate constants. Instead, it should be understood that the described techniques are provided as examples for estimating parameters; the characteristics and parameters described with respect to the techniques for estimating parameters are to be construed with the broadest sense to include variations of the particular characteristics and parameters. For example, the techniques may be used to determine a value for a rate of production of a protein (e.g., an enzyme in a metabolic pathway), which may be used to additionally or alternatively constrain the model.

ADDITIONAL CONSIDERATIONS

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium", "storage" or "memory" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A system comprising:
one or more data processors; and
a non-transitory computer readable storage medium containing instructions which, when executed on the one or more data processors, cause the one or more data processors to perform actions including:
determining, for a culture system, a dilution cycle with a predetermined period and a desired optical density;
measuring, for the dilution cycle, an actual optical density of a culture chamber of the culture system;
determining, for the culture chamber, a dilution rate as a function between the desired optical density and the actual optical density;
controlling a pump, a valve, or a combination thereof to provide fresh medium to the culture chamber at the dilution rate to return a turbidity of a biological system to the desired optical density;
measuring, by an analyzer, a characteristic of one or more characteristics in a sample of the biological system from the culture chamber to obtain at least a portion of measurement data;
obtaining the measurement data for the one or more characteristics of the biological system developed in the culture system, wherein the measurement data is indicative of each of the one or more characteristics at a physiological steady state where growth of the biological system is occurring at a substantially constant growth rate, and wherein the obtaining the measurement data comprises retrieving the portion of the measurement data from the analyzer;
determining a value for a parameter of a model of the biological system based on a growth formula, the measurement data, and the substantially constant growth rate, wherein the model predicts a response of the biological system to a set of conditions based on a plurality of parameters including the parameter, and the parameter models an aspect of structure or function of the biological system; and
parametrizing the model with at least the value determined for the parameter.

2. The system of claim 1, wherein the actions further include:
prior to determining the value for the parameter, analyzing the model of the biological system to identify the parameter as having an unknown value and as being tied to a module used to model one or more biological processes of the biological system; and
determining the one or more characteristics of the biological system that are associated with the identified parameter and are measurable in the culture system, and
wherein the parameterizing the model comprises: (i) identifying, for the module, one or more simulation parameters including the parameter, (ii) inputting the value for the parameter into the model, and (iii) fixing the value for the parameter across time-step iterations.

3. The system of claim 2, wherein the actions further include running a simulation assigned to the module of the model using an input data set and at least the value determined for the parameter to simulate at least a portion of the model of the biological system.

4. The system of claim 1, wherein the culture system is a turbidostat, and the one or more characteristics are measured after at least one dilution cycle and the predetermined period is at least 10 cell doublings.

5. The system of claim 1, wherein the actions further include:
determining the substantially constant growth rate based on a growth curve of the biological system plotted using optical density measurements of the culture system across time; and
generating the growth formula to scale at a same rate as the substantially constant growth rate, which allows for the value of the parameter to be determined without a time component or a relaxation time.

6. The system of claim 5, wherein the measurement data is obtained from a same sample of the biological system developed in the culture system, the measurement data includes the optical density measurements of the culture system, and the one or more characteristics include: (i) the substantially constant growth rate, and (ii) at least one of the following: RNA sequencing, total cellular protein, total cellular RNA, total cellular DNA, and dry cell weight.

7. A computer-implemented method comprising:
- determining, for a culture system, a dilution cycle with a predetermined period and a desired optical density;
- measuring, for the dilution cycle, an actual optical density of a culture chamber of the culture system;
- determining, for the culture chamber, a dilution rate as a function between the desired optical density and the actual optical density;
- controlling a pump, a valve, or a combination thereof to provide fresh medium to the culture chamber at the dilution rate to return a turbidity of a biological system to the desired optical density;
- measuring, by an analyzer, a characteristic of one or more characteristics in a sample of the biological system from the culture chamber to obtain at least a portion of measurement data;
- obtaining the measurement data for the one or more characteristics of the biological system developed in the culture system, wherein the measurement data is indicative of each of the one or more characteristics at a physiological steady state where growth of the biological system is occurring at a substantially constant growth rate, and wherein the obtaining the measurement data comprises retrieving the portion of the measurement data from the analyzer;
- determining a value for a parameter of a model of the biological system based on a growth formula, the measurement data, and the substantially constant growth rate, wherein the model predicts a response of the biological system to a set of conditions based on a plurality of parameters including the parameter, and the parameter models an aspect of structure or function of the biological system; and
- parametrizing the model with at least the value determined for the parameter.

8. The method of claim 7, further comprising:
- prior to determining the value for the parameter, analyzing the model of the biological system to identify the parameter as having an unknown value and as being tied to a module used to model one or more biological processes of the biological system; and
- determining the one or more characteristics of the biological system that are associated with the identified parameter and are measurable in the culture system, and
- wherein the parameterizing the model comprises: (i) identifying, for the module, one or more simulation parameters including the parameter, (ii) inputting the value for the parameter into the model, and (iii) fixing the value for the parameter across time-step iterations.

9. The method of claim 8, further comprising running a simulation assigned to the module of the model using an input data set and at least the value determined for the parameter to simulate at least a portion of the model of the biological system.

10. The method of claim 7, wherein the culture system is a turbidostat, and the one or more characteristics are measured after at least one dilution cycle and the predetermined period is at least 10 cell doublings.

11. The method of claim 7, further comprising:
- determining the substantially constant growth rate based on a growth curve of the biological system plotted using optical density measurements of the culture system across time; and
- generating the growth formula to scale at a same rate as the substantially constant growth rate, which allows for the value of the parameter to be determined without a time component or a relaxation time.

12. The method of claim 11, wherein the measurement data is obtained from a same sample of the biological system developed in the culture system, the measurement data includes the optical density measurements of the culture system, and the one or more characteristics include: (i) the substantially constant growth rate, and (ii) at least one of the following: RNA sequencing, total cellular protein, total cellular RNA, total cellular DNA, and dry cell weight.

13. A computer-program product tangibly embodied in a non-transitory machine-readable storage medium, including instructions configured to cause one or more data processors to perform actions including:
- determining, for a culture system, a dilution cycle with a predetermined period and a desired optical density;
- measuring, for the dilution cycle, an actual optical density of a culture chamber of the culture system;
- determining, for the culture chamber, a dilution rate as a function between the desired optical density and the actual optical density;
- controlling a pump, a valve, or a combination thereof to provide fresh medium to the culture chamber at the dilution rate to return a turbidity of a biological system to the desired optical density;
- measuring, by an analyzer, a characteristic of one or more characteristics in a sample of the biological system from the culture chamber to obtain at least a portion of measurement data;
- obtaining the measurement data for the one or more characteristics of the biological system developed in the culture system, wherein the measurement data is indicative of each of the one or more characteristics at a physiological steady state where growth of the biological system is occurring at a substantially constant growth rate, and wherein the obtaining the measurement data comprises retrieving the portion of the measurement data from the analyzer;
- determining a value for a parameter of a model of the biological system based on a growth formula, the measurement data, and the substantially constant growth rate, wherein the model predicts a response of the biological system to a set of conditions based on a plurality of parameters including the parameter, and the parameter models an aspect of structure or function of the biological system; and
- parametrizing the model with at least the value determined for the parameter.

14. The computer-program product of claim 13, wherein the actions further include:
- prior to determining the value for the parameter, analyzing the model of the biological system to identify the parameter as having an unknown value and as being tied to a module used to model one or more biological processes of the biological system; and
- determining the one or more characteristics of the biological system that are associated with the identified parameter and are measurable in the culture system, and
- wherein the parameterizing the model comprises: (i) identifying, for the module, one or more simulation parameters including the parameter, (ii) inputting the value for the parameter into the model, and (iii) fixing the value for the parameter across time-step iterations.

15. The computer-program product of claim 14, wherein the actions further include running a simulation assigned to the module of the model using an input data set and at least the value determined for the parameter to simulate at least a portion of the model of the biological system.

16. The computer-program product of claim 13, wherein the culture system is a turbidostat, and the one or more characteristics are measured after at least one dilution cycle and the predetermined period is at least 10 cell doublings.

17. The computer-program product of claim 13, wherein the actions further include:
- determining the substantially constant growth rate based on a growth curve of the biological system plotted using optical density measurements of the culture system across time; and
- generating the growth formula to scale at a same rate as the substantially constant growth rate, which allows for the value of the parameter to be determined without a time component or a relaxation time, and
- wherein the measurement data is obtained from a same sample of the biological system developed in the culture system, the measurement data includes the optical density measurements of the culture system, and the one or more characteristics include: (i) the substantially constant growth rate, and (ii) at least one of the following: RNA sequencing, total cellular protein, total cellular RNA, total cellular DNA, and dry cell weight.

* * * * *